(12) United States Patent
Lucci et al.

(10) Patent No.: US 11,559,238 B2
(45) Date of Patent: Jan. 24, 2023

(54) AMBULATORY MEDICAL DEVICE INCLUDING A DIGITAL FRONT-END

(71) Applicant: ZOLL Medical Corporation, Chelmsford, MA (US)

(72) Inventors: Christopher S. Lucci, Murrysville, PA (US); Nathan J. Berry Ann, Cranberry Township, PA (US); Shane S. Volpe, Saltsburg, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 311 days.

(21) Appl. No.: 16/776,724

(22) Filed: Jan. 30, 2020

(65) Prior Publication Data

US 2020/0245883 A1    Aug. 6, 2020

Related U.S. Application Data

(60) Provisional application No. 62/799,250, filed on Jan. 31, 2019.

(51) Int. Cl.
| | |
|---|---|
| *A61B 5/332* | (2021.01) |
| *A61B 5/00* | (2006.01) |
| *A61B 5/024* | (2006.01) |
| *A61B 5/282* | (2021.01) |
| *A61B 5/352* | (2021.01) |
| *A61B 5/361* | (2021.01) |
| *A61B 5/366* | (2021.01) |

(52) U.S. Cl.
CPC .......... *A61B 5/332* (2021.01); *A61B 5/02405* (2013.01); *A61B 5/282* (2021.01); *A61B 5/352* (2021.01); *A61B 5/361* (2021.01); *A61B 5/366* (2021.01); *A61B 5/7221* (2013.01)

(58) Field of Classification Search
None
See application file for complete search history.

(56) References Cited

U.S. PATENT DOCUMENTS

| | | |
|---|---|---|
| 5,944,669 A | 8/1999 | Kaib |
| 6,253,099 B1 | 6/2001 | Oskin et al. |
| 7,974,689 B2 | 7/2011 | Volpe et al. |
| 8,140,154 B2 | 3/2012 | Donnelly et al. |
| 8,600,486 B2 | 12/2013 | Kaib et al. |
| 8,676,313 B2 | 3/2014 | Volpe et al. |
| 8,706,215 B2 | 4/2014 | Kaib et al. |

(Continued)

*Primary Examiner* — Ankit D Tejani
(74) *Attorney, Agent, or Firm* — Finch & Maloney PLLC

(57) ABSTRACT

An ambulatory medical device including a plurality of sensing electrodes and one or more processors operably coupled to the plurality of sensing electrodes is provided. Each sensing electrodes is configured to be coupled eternally to a patient and to detect one or more ECG signals. The one or more processors are configured to receive at least one electrode-specific digital signal for each of the plurality of sensing electrodes, determine a noise component for each of the electrode-specific digital signals, analyze each of the noise components for each of the plurality of sensing electrodes, generate electrode matching information for each sensing electrode of the plurality of sensing electrodes based upon analysis of each of the noise components, determine one or more sensing electrode pairs based upon the electrode matching information, and monitor each of the one or more sensing electrode pairs for ECG activity of the patient.

16 Claims, 19 Drawing Sheets

(56) References Cited

U.S. PATENT DOCUMENTS

| | | | |
|---|---|---|---|
| 8,897,860 B2 | 11/2014 | Volpe et al. | |
| 2015/0313501 A1* | 11/2015 | Shachar | A61B 5/302 600/374 |
| 2016/0367162 A1* | 12/2016 | Kaib | A61B 5/316 |
| 2020/0022607 A1* | 1/2020 | Pratt | A61B 5/6891 |

* cited by examiner

AMBULATORY MEDICAL DEVICE INCLUDING A DIGITAL FRONT-END

RELATED APPLICATION

This application claims priority under 35 U.S.C. § 119(e) to U.S. Provisional Application Ser. No. 62/799,250, titled "Ambulatory Medical Device Including a Digital Front-End," filed Jan. 31, 2019. All subject matter set forth in the above-referenced application is hereby incorporated by reference in its entirety into the present application as if fully set forth herein.

BACKGROUND

The present disclosure is directed to an ambulatory medical device including a digital front-end having, for example, sensing electrodes configured to output a digital signal.

A wide variety of electronic and mechanical devices can be prescribed for monitoring and treating patients' medical conditions, such as cardiac arrhythmias. One of the deadliest cardiac arrhythmias is ventricular fibrillation (VF), which occurs when normal, regular electrical impulses are replaced by irregular and rapid impulses, causing the heart muscle to stop normal contractions. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as VF, ventricular tachycardia (VT), pulseless electrical activity (PEA), and asystole result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. VF or VT can be treated by an external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

A patient at high risk of a cardiac arrhythmia may be prescribed an ambulatory monitoring and treatment device such as the ZOLL LifeVest® wearable cardioverter defibrillator available from ZOLL Medical Corporation. The device includes one or more microprocessors that operate on digitized physiological data to assess the patient's health in accordance with predetermined criteria. For example, such physiological data can include electrocardiogram (ECG) data derived from multiple sensing electrodes in contact with the patient's skin.

SUMMARY

In at least one example, an ambulatory medical device is provided. The ambulatory medical device includes a plurality of sensing electrodes and one or more processors operably coupled to the plurality of sensing electrodes. Each of the plurality of sensing electrodes is configured to be coupled eternally to a patient and to detect one or more ECG signals. The one or more processors are configured to receive at least one electrode-specific digital signal for each of the plurality of sensing electrodes, determine a noise component for each of the electrode-specific digital signals, analyze each of the noise components for each of the plurality of sensing electrodes, generate electrode matching information for each sensing electrode of the plurality of sensing electrodes based upon analysis of each of the noise components, determine one or more sensing electrode pairs based upon the electrode matching information, and monitor each of the one or more sensing electrode pairs for ECG activity of the patient.

Implementations of such an ambulatory medical device may include one or more of the following features.

In the ambulatory medical device, the one or more processors can further be configured to determine updated noise components for each sensing electrode of the plurality of sensing electrodes, analyze each updated noise component of the updated noise components for each sensing electrode of the plurality of sensing electrodes, generate updated electrode matching information for each sensing electrode of the plurality of sensing electrodes based upon analysis of the updated noise components, and determine one or more updated sensing electrode pairs based upon the updated electrode matching information.

In the ambulatory medical device, the one or more processors can further be configured to determine a gain adjustment for one or more of the plurality of sensing electrodes to improve signal quality of at least one of the one or more sensing electrode pairs.

In the ambulatory medical device, the electrode matching information can include one or more of a signal strength ranking for each of the plurality of sensing electrodes and a signal-to-noise ratio for each of the plurality of sensing electrodes.

In the ambulatory medical device, each sensing electrode of the plurality of sensing electrodes can include an analog to digital converter (ADC) configured to receive an analog electrical signal produced by the patient and convert the analog electrical signal to the electrode-specific digital signal for each of the plurality of sensing electrodes. In some examples, each of the ADCs can be configured to sample the analog electrical signal at a dynamically adjustable sampling rate controlled by the one or more processors. In some examples, the one or more processors can further be configured to generate a common timing signal for each of the ADCs such that the ADCs are synchronized.

In the ambulatory medical device, the ECG activity can include one or more ECG metrics derived from the one or more ECG signals of the patient.

In the ambulatory medical device, the one or more ECG metrics can include at least one of heart rate, heart rate variability, PVC burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T-wave variability, and ST segment changes.

In the ambulatory medical device, the ambulatory medical device can further include therapy delivery circuitry configured to produce a therapy shock. In some examples, the ambulatory medical device can further include a plurality of therapy electrodes operably coupled to the therapy delivery circuitry and configured to be coupled to the patient to deliver the therapy shock to the patient.

In an example, an ambulatory medical device includes a plurality of sensing electrodes and one or more processors operably coupled to the plurality of sensing electrodes. Each of the plurality of sensing electrodes is configured to be coupled externally to a patient and to detect one or more ECG signals of the patient. The one or more processors are configured to receive at least one electrode-specific digital signal for each sensing electrode of the plurality of sensing electrodes, determine a noise component for each of the electrode-specific digital signals, analyze each of the noise components for each of the plurality of sensing electrodes to determine whether one or more of the plurality of sensing electrodes has a physically compromised connection with the patient, ignore at least one sensing electrode with a physically compromised connection with the patient, thereby resulting in a reduced set of sensing electrodes, and monitor ECG activity of the patient using the reduced set of sensing electrodes.

Implementations of such an ambulatory medical device may include one or more of the following features.

In the ambulatory medical device, the one or more processors can further be configured to determine updated noise components for each of the plurality of sensing electrodes, analyze each of the updated noise components for each of the plurality of sensing electrodes to determine updated connection information, determine an updated set of sensing electrodes for monitoring the patient based upon the updated connection information, and monitor ECG activity of the patient using the updated set of sensing electrodes.

In the ambulatory medical device, the one or more processors can further be configured to determine if the noise component for the at least one of the plurality of sensing electrodes with a physically compromised connection with the patient has fallen below a threshold indicating that a physical connection with the patient is no longer compromised and, where the noise component for the at least one of the plurality of sensing electrodes that has a physically compromised connection with the patient has fallen below the threshold, update a set of electrodes for monitoring the patient to include each of the plurality of sensing electrodes that have a noise component below the threshold.

In the ambulatory medical device, the one or more processors can further be configured to generate a driven ground signal based upon the noise components for each of the electrode-specific digital signals and, where at least one of the plurality of sensing electrodes has a physically compromised connection with the patient, ignore the at least one sensing electrode with a physically compromised connection with the patient during generation of the driven ground signal.

In the ambulatory medical device, the ECG activity can include one or more ECG metrics derived from the one or more ECG signals of the patient. In some examples, the one or more ECG metrics can include at least one of heart rate, heart rate variability, PVC burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T-wave variability, and ST segment changes.

In the ambulatory medical device, the ambulatory medical device can further include therapy delivery circuitry configured to produce a therapy shock. In some examples, the ambulatory medical device can include a plurality of therapy electrodes operably coupled to the therapy delivery circuitry and configured to be coupled to the patient to deliver the therapy shock to the patient.

In an example, an ambulatory medical device includes a plurality of sensing electrodes and one or more processors operably coupled to the plurality of sensing electrodes. Each of the plurality of sensing electrodes is configured to be coupled externally to a patient and to detect one or more ECG signals of the patient. The one or more processors are configured to cause a bio-impedance signal to be generated by at least a portion of the ambulatory medical device and delivered to the patient, adjust a frequency of the bio-impedance signal such that the bio-impedance signal sweeps through a range of predetermined signal frequencies, receive at least one electrode-specific digital signal for each of the plurality of sensing electrodes, the at least one electrode-specific digital signal comprising at least one portion comprising a measured response to each of the predetermined signal frequencies of the bio-impedance signal, derive a bio-impedance value for each of the plurality of sensing electrodes based upon the measured response to each of the predetermined signal frequencies of the bio-impedance signal, analyze each of the bio-impedance values to determine an impedance value for each sensing electrode of the plurality of sensing electrodes, and determine localized skin response for the patient at each of the plurality of sensing electrodes based upon the impedance values for each of the plurality of sensing electrodes.

Implementations of such an ambulatory medical device may include one or more of the following features.

In the ambulatory medical device, the one or more processors can further be configured to generate an impedance model of the patient for each sensing electrode of the plurality of sensing electrodes and adjust a signal received from each sensing electrode of the plurality of sensing electrodes based upon an associated impedance model.

In the ambulatory medical device, the one or more processors can further be configured to determine at least one hydration level for the patient based upon the localized skin response for the patient at each sensing electrode of the plurality of sensing electrodes.

In the ambulatory medical device, the one or more processors can further be configured to cause at least a portion of the ambulatory medical device to output one or more instructions to the patient based upon the localized skin response for the patient at each sensing electrode of the plurality of sensing electrodes. In some examples, the one or more instructions can include at least one of instruct the patient to adjust a position of at least one of the plurality of sensing electrodes and instruct the patient to apply conductive gel to at least one of the plurality of sensing electrodes.

In the ambulatory medical device, the ambulatory medical device can further include therapy delivery circuitry configured to produce a therapy shock. In some examples, the ambulatory medical device can include a plurality of therapy electrodes operably coupled to the therapy delivery circuitry and configured to be coupled to the patient to deliver the therapy shock to the patient.

In an example, an ambulatory medical device includes a plurality of motion detectors, a plurality of sensing electrodes, and one or more processors operably coupled to the plurality of sensing electrodes and being configured to. Each of the plurality of sensing electrodes is configured to be coupled externally to a patient and to detect one or more ECG signals of the patient and includes one of the plurality of motion detectors. The one or more processors are configured to receive at least one electrode-specific digital signal for each sensing electrode of the plurality of sensing electrodes, wherein at least a portion of each electrode-specific digital signal includes motion information measured by each motion detector included within the sensing electrode, determine a motion value for each of the plurality of sensing electrodes based upon the motion information, adjust at least one operational parameter for the ambulatory medical device based upon the determined motion values, and monitor the one or more ECG signals for ECG activity of the patient using the adjusted at least one operational parameter.

Implementations of such an ambulatory medical device may include one or more of the following features.

In the ambulatory medical device, the one or more processors can be configured to adjust at least one operational parameter for the ambulatory medical device based upon the determined motion values by determining whether one or more of the motion values for each sensing electrode of the plurality of sensing electrodes exceeds a threshold and, where one or more of the motion values for at least one sensing electrodes exceeds a threshold, adjusting the at least one operational parameter for the ambulatory medical device. In some examples, the one or more processors can be configured to ignore each of the plurality of sensing electrodes having a motion value that exceeds the threshold.

In the ambulatory medical device, the one or more processors can further be configured to determine if at least a portion of the monitored ECG signals indicates an adverse cardiac event occurrence and analyze the motion information to determine if the adverse cardiac event includes a false reading resulting from movement of at least one of the plurality of sensing electrodes.

In the ambulatory medical device, the ECG activity for the patient can include one or more ECG metrics derived from the one or more ECG signals of the patient. In some examples, the one or more ECG metrics can include at least one of heart rate, heart rate variability, PVC burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T-wave variability, and ST segment changes.

In the ambulatory medical device, the ambulatory medical device can include a therapy delivery circuitry configured to produce a therapy shock. In some examples, the ambulatory medical device can include a plurality of therapy electrodes operably coupled to the therapy delivery circuitry and configured to be coupled to the patient to deliver the therapy shock to the patient.

In an example, an ambulatory medical device includes a plurality of sensing electrodes and one or more processors operably coupled to the plurality of sensing electrodes. Each of the plurality of sensing electrodes is configured to be coupled to a patient and to detect one or more ECG signals of the patient and includes at least one contact surface configured to be coupled to the patient and collect electrical signals from the patient, a digital converter operably connected to the at least one contact surface and configured to convert the collected electrical signals to an electrode-specific digital signal, and at least one electrode processor operably connected to the digital converter and configured to control a sampling rate of the digital converter. The or more processors are configured to receive the electrode-specific digital signal from each of the plurality of sensing electrodes, analyze each of the electrode-specific digital signals, determine one or more sensing electrode pairs based upon analysis of each of the electrode-specific digital signals, and monitor each of the one or more sensing electrode pairs for ECG activity of the patient.

Implementations of such an ambulatory medical device may include one or more of the following features.

In the ambulatory medical device, the one or more processors can be configured to receive the electrode-specific digital signal from each of the plurality of sensing electrodes, determine a noise component for each of the electrode-specific digital signals, wherein each of the plurality of sensing electrodes has an associated noise component, analyze each of the noise components for each of the plurality of sensing electrodes, generate electrode matching information for each sensing electrode of the plurality of sensing electrodes based upon analysis of each of the noise components, determine one or more sensing electrode pairs based upon the electrode matching information, and monitor each of the one or more sensing electrode pairs for ECG activity of the patient.

In the ambulatory medical device, the one or more processors can be configured to receive the electrode-specific digital signal from each of the plurality of sensing electrodes, determine a noise component for each of the electrode-specific digital signals, wherein each of the plurality of sensing electrodes has an associated noise component, analyze each of the noise components for each of the plurality of sensing electrodes to determine whether one or more of the plurality of sensing electrodes has a physically compromised connection with the patient, ignore at least one sensing electrode with a physically compromised connection with the patient, thereby resulting in a reduced set of sensing electrodes, and monitor ECG activity of the patient using the reduced set of sensing electrodes.

In the ambulatory medical device, the ECG activity can include one or more ECG metrics derived from the one or more ECG signals of the patient. In some examples, the one or more ECG metrics can include at least one of heart rate, heart rate variability, PVC burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T-wave variability, and ST segment changes.

In the ambulatory medical device, the ambulatory medical device can further include therapy delivery circuitry configured to produce a therapy shock. In some examples, the ambulatory medical device can include a plurality of therapy electrodes operably coupled to the therapy delivery circuitry and configured to be coupled to the patient to deliver the therapy shock to the patient.

In an example, a method is provided. The method includes providing by an ambulatory medical device a plurality of sensing electrodes configured to be coupled externally to a patient and to detect one or more ECG signals of the patient. Such method includes receiving, by one or more processors operably coupled to the plurality of sensing electrodes, at least one electrode-specific digital signal for each of the plurality of sensing electrodes, determining a noise component for each of the electrode-specific digital signals, analyzing each of the noise components for each of the plurality of sensing electrodes, generating electrode matching information for each sensing electrode of the plurality of sensing electrodes based upon analysis of each of the noise components, determining one or more sensing electrode pairs based upon the electrode matching information, and monitoring each of the one or more sensing electrode pairs for ECG activity of the patient.

In an example, a method includes providing by an ambulatory medical device a plurality of sensing electrodes configured to be coupled externally to a patient and to detect one or more ECG signals of the patient. Such method includes receiving, by one or more processors operably coupled to the plurality of sensing electrodes, at least one electrode-specific digital signal for each sensing electrode of the plurality of sensing electrodes, determining a noise component for each of the electrode-specific digital signals, analyzing each of the noise components for each of the plurality of sensing electrodes to determine whether one or more of the plurality of sensing electrodes has a physically compromised connection with the patient, ignoring at least one sensing electrode with a physically compromised connection with the patient, thereby resulting in a reduced set of sensing electrodes, and monitoring ECG activity of the patient using the reduced set of sensing electrodes.

In an example, a method includes providing by an ambulatory medical device a plurality of sensing electrodes configured to be coupled externally to a patient and to detect one or more ECG signals of the patient. The method includes causing, by one or more processors operably coupled to the plurality of sensing electrodes, a bio-impedance signal to be generated by at least a portion of the ambulatory medical device and delivered to the patient, adjusting a frequency of the bio-impedance signal such that the bio-impedance signal sweeps through a range of predetermined signal frequencies, receiving at least one electrode-specific digital signal for each of the plurality of sensing electrodes, the at least one electrode-specific digital signal comprising at least one portion comprising a measured response to each of the predetermined signal frequencies of the bio-impedance signal, deriving a bio-impedance value for each of the plurality of sensing electrodes based upon the measured response to each of the predetermined signal frequencies of the bio-impedance signal, analyzing each of the bio-impedance values to determine an impedance value for each sensing electrode of the plurality of sensing electrodes, and determining localized skin response for the patient at each of the plurality of sensing electrodes based upon the impedance values for each of the plurality of sensing electrodes.

In an example, a method includes providing by an ambulatory medical device a plurality of motion detectors, and a plurality of sensing electrodes configured to be coupled externally to a patient and to detect one or more ECG signals of the patient, each sensing electrode of the plurality of sensing electrodes comprising a motion detector of the plurality of motion detectors. Such method includes receiving, by one or more processors operably coupled to the plurality of sensing electrodes, at least one electrode-specific digital signal for each sensing electrode of the plurality of sensing electrodes, wherein at least a portion of each electrode-specific digital signal comprises motion information measured by each motion detector comprised within the sensing electrode, determining a motion value for each of the plurality of sensing electrodes based upon the motion information, adjusting at least one operational parameter for the ambulatory medical device based upon the determined motion values, and monitoring the one or more ECG signals for ECG activity of the patient using the adjusted at least one operational parameter.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1A:
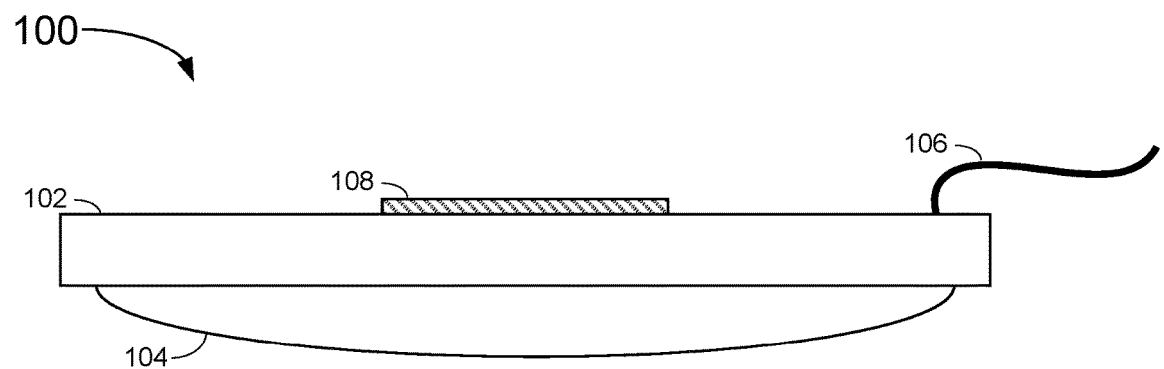
FIG. 1A depicts a side view of a digital sensing electrode, in accordance with an example of the present disclosure.

Medical devices such as patient monitoring and/or treatment devices monitor and record various physiological or vital signals via one or more sensing electrodes that are coupled externally to a patient's skin. Conventionally, a cardiac monitoring and/or treatment device can monitor and record electrocardiogram (ECG) signals via ECG sensing electrodes that are adapted for external attachment or coupling to the skin of the patient. These sensing electrodes acquire physiological electrical signals in analog form that are descriptive of the physiology of the patient. In implementations, the physiological electrical signals include cardiac electrical signals that are descriptive of the cardiac activity in the patient and sensed on the patient's skin. Such sensing electrodes can include, for example, a contact surface, a high impedance buffer circuit including a buffer amplifier to accommodate signals from a high impedance source such as an electrode contact surface and the patient's skin and other processing components, and a transmission conduit such as a wire for carrying the analog signal to a microprocessor or some other processor for additional processing. Cardiac monitoring and/or treatment devices that include sensing electrodes of this sort further include circuitry that operates on the analog signals acquired by the electrodes. For example, such operations may be performed by processing circuitry housed within a medical device monitor and/or controller device that may be coupled via one or more cables to the sensing electrode(s). These operations may, for example, condition and/or combine the analog signals from each sensing electrode for a variety of reasons prior to digitizing the signals. In some scenarios, the signals may be digitized by an analog to digital converter located remotely from the sensing electrodes such as within the medical device monitor and/or controller device. Other signal operations that can be performed include summing of the analog signals acquired by the sensing electrodes to create a common mode noise signal used as a driven ground to be fed back into the patient using, in certain examples, a driven right leg circuit. Additional operations can include signal filtering, electrode falloff detection, noise detection and/or correction, and other similar signal processing operations. As with the digitizing operations, such other operations may be performed by processing circuitry housed within the medical device monitor and/or controller device coupled via one or more cables to the sensing electrode(s).

In this disclosure, Applicants describe systems and techniques to address certain disadvantages inherent in conventional ECG sensors. For example, there can be powerline interference on the cables or wires carrying the analog signals which creates transmission noise on the analog signals as a result of, for example, a field coupling effect. Additionally, if one of the sensing electrodes experiences a falloff event (e.g., a sensing electrode loses electrical contact with the patient's body or the physical sensor connection with the patient's body is otherwise compromised), noise created on that sensing electrode can be included when calculating the driven ground signal for the driven right leg circuit, resulting in an unreliable or inaccurate driven ground. An unreliable reference for common mode such as driven ground based on, for example, Wilson's central terminal or a right leg drive, can affect the accuracy of the ECG information derived by the ECG circuitry.

Thus, and in accordance with various examples disclosed herein, Applicants have developed digital front-end circuitry, systems, techniques, and methods for use with cardiac monitoring and/or treatment devices.

For example, the digital front-end can be characterized by including one or more digital sensing electrodes configured to be positioned adjacent and coupled to the patient's skin and to output an electrode-specific digital signal related to measured electrical activity for the patient. The digital sensing electrodes can house multiple digital circuit components (e.g., a plurality of amplifiers, op-amps, signal converters, comparators, timing circuits, signal synthesizers, sensors, and/or one or more microprocessors or microcontrollers) arranged and configured to convert a measured cardiac analog signal obtained from the patient to a digital signal for output from the digital sensing electrodes. These electrode-specific digital signals may be further processed by, for example, a monitoring device operably coupled to the digital sensing electrode. Each digital sensing electrode is thus able to produce electrode-specific digital signals that are made available to the monitoring device for further processing, including arrhythmia detection.

Using a digital front-end including multiple digital sensing electrodes with an ambulatory medical device provides several advantages. For example, by providing each digital sensing electrode output as an electrode-specific digital signal, the electrodes can be paired, and their signals summed in any combination in a dynamic manner rather than the predesigned hard-wired electrode pairings inherent in conventional ECG systems. Another advantage is reduction of noise artifacts due to an electrode falling off a patient or otherwise making poor electrical contact with the patient's skin. If a noise artifact is detected, a corresponding electrode-specific digital signal can be digitally processed to remove the noise specific to the electrode. In some implementations, the corresponding electrode-specific digital signal may be removed or otherwise ignored in further processing. As an example, the electrode-specific signals are summed to generate a common mode signal for use in minimizing or eliminating interference effects common to all the electrodes. In an instance where a noise artifact is detected, the corresponding electrode-specific digital signal can be dropped the from the common mode interference determination as described below. Such an approach reduces unwanted noise being fed back into the patient using, for example, Wilson's central terminal or a right leg drive circuit.

To implement such functionality, each digital sensing electrode can include analog processing circuitry for processing the physiological analog signal picked up by the electrode contact surface and corresponding digital processing circuitry to process such a physiological signal. In one implementation described in further detail below, one or more of the digital sensing electrodes can each physically house both the analog and digital circuitries to process the physiological signal picked up from the skin of the patient and convert the signal to electrode-specific digital signals. In examples, the digital circuitry can include an analog-to-digital converter (ADC) to convert the physiological signal from analog form to the electrode-specific digital signal. The electrode-specific digital signal can then be further processed by, for example, a microprocessor prior to being transmitted from the digital sensing electrode to a monitoring device for further processing. In examples, the microprocessor can control the operation of the ADC based in turn on instructions received from one or more processors in a cardiac monitoring and/or treatment device coupled to the digital sensing electrodes. In this regard, the microprocessor operates based on instructions encoded thereon and a plurality of parameters that can be configurable by an operator via an interface.

In some examples, the analog and digital circuitries corresponding to each digital sensing electrode may be housed separately. For instance, the digital processing circuitry including the ADC and microprocessor may be disposed within a separate housing from the analog processing circuitry.

The digital front-end, including the digital sensing electrodes, as described herein can vary depending upon the implementation of the ambulatory medical device. In an example, a digital sensing electrode includes a skin-contacting electrode surface coupled to the multiple digital circuit components as described further herein and disposed within a housing. Such digital circuit components can include an integrated microprocessor configured to receive instructions from the monitoring device to control the functionality of the digital sensing electrode. For example, the integrated microprocessor can receive a signal to control a sampling rate for an associated ADC. In another example, the integrated microprocessor can receive a signal to adjust the gain of the electrode-specific digital signal prior to transmitting to the monitoring device for further processing.

In an example, an ambulatory medical device including a digital front-end as described herein can include multiple digital sensing electrodes configured to be coupled to a patient to detect one or more ECG signals of the patient. Each of the digital sensing electrodes can include at least one contact surface, a digital converter, and at least one microprocessor. The at least one contact surface can be configured to be positioned adjacent and coupled to the patient and collect electrical signals from the patient. The digital converter can be operably connected to the at least one contact surface and configured to convert the collected electrical signals to an electrode-specific digital signal. The at least one microprocessor can be operably connected to the digital converter and configured to control a sampling rate of the digital converter. The ambulatory medical device can further include one or more processors disposed remotely from and operably coupled to the digital sensing electrodes. These one or more processors can be configured to receive the electrode-specific digital signals from each of the digital sensing electrodes, analyze each of the electrode-specific digital signals, determine one or more digital sensing electrode pairs based upon analysis of each of the electrode-specific digital signals, and monitor each of the one or more digital sensing electrode pairs for ECG activity of the patient.

An ambulatory medical device with a digital front-end as described herein can implement several features. In certain implementations, an ambulatory medical device can change digital sensing electrode pairs based upon real-time noise information for the digital sensing electrodes. For example, an ambulatory medical device can include multiple digital sensing electrodes and one or more processors. The multiple digital sensing electrodes can be configured to be coupled to a patient and to detect one or more ECG signals of the patient. The one or more processors can be operably coupled to the digital sensing electrodes. The one or more processors can be configured to receive at least one electrode-specific digital signal for each of the digital sensing electrodes and determine a noise component for each of the electrode-specific digital signals. The one or more processors can be further configured to analyze each of the noise components, determine one or more matching digital sensing electrodes based upon analysis of each of the noise components and generate electrode matching information. Based upon the electrode matching information, the one or more processors can be configured to determine one or more digital sensing electrode pairs and monitor each of the one or more digital sensing electrode pairs for ECG activity of the patient. In implementations, the one or more processors operates based on instructions encoded thereon and a plurality of parameters that can be configurable by an operator via an interface.

In examples, another potential feature of an ambulatory medical device with a digital front-end as described herein is determining whether one or more digital sensing electrodes have a physically compromised connection with the patient. For example, an ambulatory medical device can include multiple digital sensing electrodes and one or more processors operably coupled to the digital sensing electrodes. The digital sensing electrodes can be configured to be coupled to a patient and to detect one or more ECG signals of the patient. The one or more processors can be configured to receive at least one electrode-specific digital signal for each of the digital sensing electrodes and determine a noise component for each of the electrode-specific digital signals. The one or more processors can be further configured to analyze each of the noise components to determine whether one or more of the digital sensing electrodes has a physically compromised connection with the patient. The one or more processors can be further configured to ignore any digital sensing electrode with a physically compromised connection with the patient, thereby resulting in a reduced set of digital sensing electrodes, and monitor ECG activity of the patient using the reduced set of digital sensing electrodes.

In some implementations, another potential feature of an ambulatory medical device with a digital front-end as described herein is determining bio-impedance information such as localized skin response for a patient. For example, an ambulatory medical device can include multiple digital sensing electrodes and one or more processors operably coupled to the digital sensing electrodes. The digital sensing electrodes can be configured to be coupled to a patient and to detect one or more ECG signals of the patient. The one or more processors can be configured to cause a bio-impedance signal to be generated by at least a portion of the ambulatory medical device and delivered to the patient. The one or more processors can further be configured to adjust a frequency of the bio-impedance signal such that the bio-impedance signal sweeps through a range of predetermined signal frequencies and receive at least one electrode-specific digital signal for each of the digital sensing electrodes, the at least one electrode-specific digital signal comprising at least one portion that includes a measured response to each of the predetermined signal frequencies of the bio-impedance signal. The one or more processors can be further configured to derive a bio-impedance value, or a surrogate signal related to this information, for each of the digital sensing electrodes based upon the measured response to each of the predetermined signal frequencies of the bio-impedance signal, analyze each of the bio-impedance values to determine an impedance value for each of the digital sensing electrodes, and determine localized skin response for the patient at each of the digital sensing electrodes based upon the impedance values for each of the digital sensing electrodes.

Further, a potential feature of an ambulatory medical device with a digital front-end as described herein can include determining localized motion information for each of the digital electrodes and adjusting operation of the medical device accordingly. For example, an ambulatory medical device can include multiple digital sensing electrodes, each digital sensing electrode including at least one integrated motion detector, and one or more processors operably coupled to the digital sensing electrodes. The digital sensing electrodes can be configured to be coupled to a patient and to detect one or more ECG signals of the patient. The one or more processors can be configured to receive at least one electrode-specific digital signal for each of the digital sensing electrodes, wherein at least a portion of each electrode-specific digital signal includes motion information measured by at least one of the motion detectors for an associated digital sensing electrode. The one or more processors can be further configured to determine a motion value for each of the digital sensing electrodes based upon the motion information, adjust at least one operational parameter for the ambulatory medical device based upon the determined motion values, and monitor the one or more ECG signals of the patient using the adjusted at least one operational parameter.

These examples, and various other similar examples of benefits and advantages of the techniques, processes, and approaches as provided herein, are described in additional detail below.

As noted herein, patient monitoring and treatment devices are used to monitor and record various physiological or vital signals for a patient and provide treatment to a patient when necessary. For patients at risk of a cardiac arrhythmia, specialized cardiac monitoring and/or treatment devices such as a cardiac event monitoring device, a wearable cardioverter defibrillator (WCD), or a hospital wearable defibrillator can be prescribed to and worn by the patient for an extended period of time. For example, a patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed a specialized cardiac monitoring and/or treatment device.

For example, a WCD such as the LifeVest® Wearable Cardioverter Defibrillator from ZOLL Medical Corporation (Chelmsford, Mass.), can be prescribed to the patient. As described in further detail below, such a device includes a garment that is configured to be worn about the torso of the patient. The garment can be configured to house various components such as ECG sensing electrodes and therapy electrodes. The components in the garment can be operably connected to a monitoring device that is configured to receive and process signals from the ECG sensing electrodes to determine a current cardiac condition of the patient and, if necessary, provide treatment to the patient using the therapy electrodes.

Figure 1B:
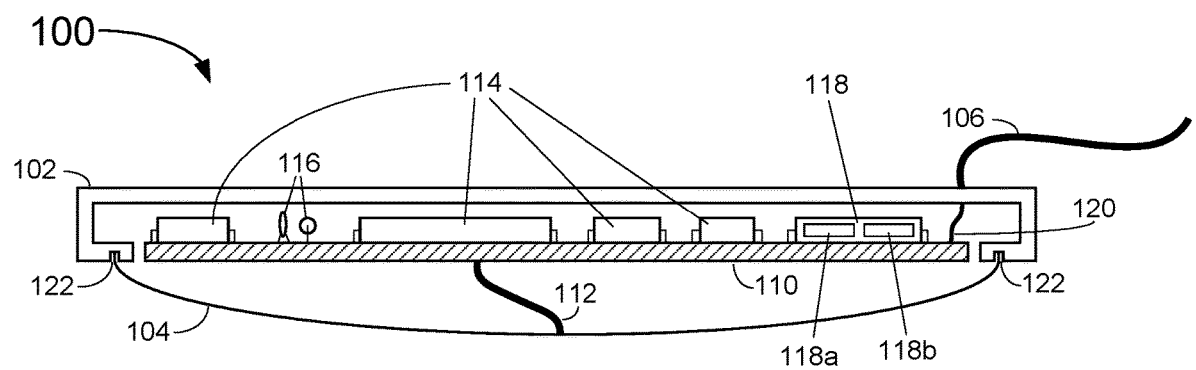
FIG. 1B depicts a side, cross-sectional view of a digital sensing electrode, in accordance with an example of the present disclosure.

In an ambulatory medical device, an electrode such as an ECG sensing electrode can be configured to operate as a digital sensing electrode in a digital front-end for an ambulatory medical device such as a WCD. The digital sensing electrode can include a portion configured to contact the skin of a patient and acquire physiological signals generated by the patient (e.g., collected as analog electrical signals). FIGS. 1A and 1B illustrate sample views of a digital sensing electrode 100 as described herein.

As shown in FIG. 1A, the digital sensing electrode 100 can include a housing 102 configured to enclose various electrical components and other electrode components. The housing 102 can be manufactured from a polymer such as polyethylene or polyvinylchloride using, for example, a casting or a molding manufacturing process. The digital sensing electrode 100 can also include a skin-contacting portion 104 attached to the housing 102. As shown in FIG. 1A, the skin-contacting portion 104 can have a dome shape that improves the electrode-skin interface by providing for contact surface even if the digital sensing electrode 100 is angled or otherwise rotated partially away from the patient's skin. The skin-contacting portion 104 is shown as having a dome shape by way of example only. Other shapes can be used. Similarly, a degree of convexity of the dome shape can be changed depending upon the anticipated movement and/or rolling of the digital sensing electrode 100 when being worn by the patient.

In certain implementations, the skin-contacting portion 104 can be made from a metal that is pressed into shape using, for example, a hydraulic press manufacturing technique. In some examples, the skin-contacting portion 104 can be made from a relatively non-corroding material such as stainless steel. In other examples, the skin-contacting portion 104 can be made from a metal compound such as silver-silver chloride (Ag—AgCl). In certain implementations, the skin-contacting portion can include an oxide coating (e.g., an oxide coating having a high dielectric constant) preferably formed over the entire contacting surface. For example, the skin-contacting portion 104 can be made from tantalum metal and have a tantalum pentoxide coating. For example, the skin-contacting portion 104 can be constructed as described in U.S. Pat. No. 6,253,099 entitled "Cardiac Monitoring Electrode Apparatus and Method," the content of which is incorporated herein by reference in its entirety.

As further shown in FIG. 1A, the digital sensing electrode 100 can include a wire 106 configured to electrically couple the digital sensing electrode to another electrode and/or a monitoring device. The wire 106 can include a copper, aluminum, or other similar conductive metal core coated in rubber or another similar flexible insulating material. Alternatively, the wire 106 can include a non-conductive core plated or otherwise covered with a conductive surface. The wire 106 can be configured to pass through the housing 102 to access one or more electrical components contained within the housing. In certain implementations, an access point through the housing 102 can be sealed with a flexible rubber gasket or other similar sealing material to maintain the integrity of the housing.

In some examples, the digital sensing electrode 100 can include a fastening device 108 attached to a surface of the housing 102 and configured to removably attach the electrode to a garment, belt, or other supporting structure to be worn by a patient such that the digital sensing electrode is positioned and held in contact with, or coupled to, the patient's skin. In certain implementations, the fastening device can include a hook and loop fastener, a snap fastener, an adhesive fastener, and other similar reusable fastening devices. In certain applications, the digital sensing electrode 100 may be permanently attached to an inner fabric of the garment worn by the patient.

FIG. 1B illustrates a cross-sectional view of the digital sensing electrode. As shown in FIG. 1B, the housing 102 can be sized and configured to receive a printed circuit board (PCB) 110. The PCB 110 can be electrically coupled to the skin-contacting portion 104 with a wire 112. In certain implementations, the wire 112 can be securely fastened to the skin-contacting portion 104 by, for example, welding or soldering to provide a secure attachment that can withstand vibrations, movement and possible deformation of the digital sensing electrode 100 during normal use.

As shown in FIG. 1B, the PCB 110 can include various circuit components 114. For example, the various circuit components can include an analog buffer stage, amplifiers, surge protection circuitry, an ADC, a microprocessor, and other similar circuit components. A more detailed explanation of the circuitry components is included in the discussion of FIGS. 4A and 4B below. In certain implementations, the PCB 110 can include additional electrical components 116 such as resistors, capacitors, inductors, diodes, and other similar electrical components included to condition or otherwise alter the electrical signals passing through the PCB.

In certain implementations, the PCB 110 can further include sensors 118 such as environmental sensors, motion sensors, and/or additional sensors. For example, the sensors 118 can include environmental sensors 118a such as temperature and humidity sensors configured to measure environmental conditions such as temperature and humidity. The sensors 118 can also include motion sensors 118b such as a gyroscope or a three-axis accelerometer configured to measure movement of the digital sensing electrode 100 in three dimensions (e.g., along an X-axis, a Y-axis, and a Z-axis). For instance, examples of motion sensors 118b include multi-axis accelerometers and multi-axis gyroscopes, such as the ADIS16362 iSensor® inertial system from ANALOG DEVICES®, or the iNEMO® M1 motion sensing system manufactured by STMicroelectronics® (which also includes a multi-axis magnetometer). Motion information, as measured by the sensors 118, can be used to monitor movement of the digital sensing electrode 100 and account for any motion artifacts in physiological signals collected by the digital sensing electrode as described below in the discussion of FIGS. 8A-8C. The sensors 118 can also include additional sensors such as acoustic sensors and bio-vibrational sensors configured to measure, for example, heart sounds, lung sounds, and other bio-acoustic and/or bio-vibrational signals.

The output of the circuitry included on the PCB 110 can be passed through internal wire 120 to the wire 106 for transmission to, for example, a monitoring device or another processor operably connected to the digital sensing electrode 100.

In some implementations, the skin-contacting portion 104 operates at a high impedance relative to the patient's skin. For example, depending upon the patient, the impedance at the patient's skin can range from approximately 100 Kilo-ohms to one or more megaohms in, for example, an ECG bandwidth of about 0.5 Hz to about 150 Hz. Typically, depending upon skin condition and other similar factors, as signal frequency increases a measurable impedance at the electrode-skin interface decreases. Conversely, as signal frequency decreases, the measurable impedance at the electrode-skin interface increases.

In some examples, the analog buffer stage on the PCB 110 of the digital sensing electrode 100 can include a buffer amplifier to condition and increase the associated input impedance so that the amplifier input impedance does not unduly compromise signal fidelity and/or integrity. The output of this buffer amplifier can be a relatively low impedance signal (compared to, for example, the input impedance) allowing ease of processing. The analog to digital conversion process is also described in greater detail below in the discussion of FIGS. 4A and 4B.

In certain implementations, depending upon the application of the digital sensing electrode 100, the housing 102 and the skin-contacting portion 104 can be affixed to provide a sealed enclosure having a pre-designed ingress rating. For example, as shown in FIG. 1B, an outer edge of the skin-contacting portion 104 can be configured to fit within a notch 122 in the housing 102. The edge of the skin-contacting portion 104 can be adhered using an epoxy resin within the notch 122, thereby providing a sealed fit with the housing 102. In certain implementations, the digital sensing electrode 100 can be tested and assigned an International Protection Marking (IP) Code, sometimes referred to as an Ingress Protection Marking, as defined by IEC standard 60529, which classifies and rates the degree of protection provided against intrusion by dust and water for mechanical casings and enclosures. For example, if digital sensing electrode 100 is designed to provide complete protection from dust and be submersible in water up to one meter in depth, the electrode can be assigned an IP Code of IP67, where the 6 represent protection from dust ingress and the 7 represents submersion in water up to one meter.

The design of the digital sensing electrode 100 as shown in FIGS. 1A and 1B is for illustrative purposes only. For example, the geometric shapes of the components such as the housing 102 and the skin-contacting portion 104 are provided for illustration. Alternative shapes and sizes can be used when designing the digital sensing electrode 100. Additionally, the individual electrical and circuit components 114 and 116 as well as the sensors 118 can vary based upon the designed functionality of the electrode and design of the PCB 110.

Further, in some implementations, the digital processing circuitry can be physically located within a separate housing from the housing 102. In such implementations, the separate housing may also include a second PCB that is mechanically secured within the separate housing. The second PCB can have disposed thereon (e.g., via soldering) digital processing components including the ADC and associated integrated microprocessor.

Figure 1C:
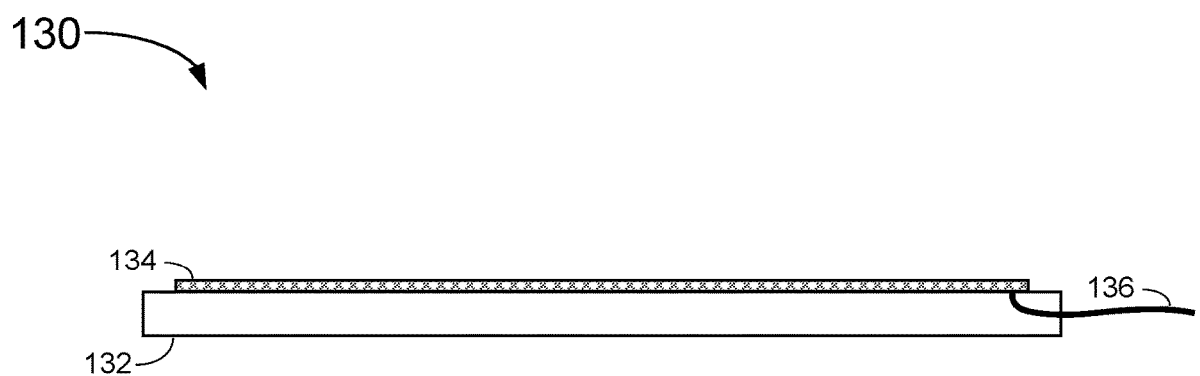
FIG. 1C depicts an alternative digital sensing electrode design, in accordance with an example of the present disclosure.

For example, as shown in FIG. 1C, a digital electrode can be designed as a textile digital sensing electrode 130. The textile digital sensing electrode 130 can include one or more layers of fabric 132. For example, the fabric 132 can be a part of a garment associated with an ambulatory medical device and configured to be worn by the patient. The fabric 132 can include one or more layers of natural and/or artificial fibers that are woven, adhered, or otherwise attached to form a flexible layer. In some examples, the fabric 132 can include multiple layers of different materials designed and arranged to provide comfort to the patient wearing the ambulatory medical device. For example, the layer of the fabric 132 that is next to the patient's skin can be made form a wicking material to absorb sweat and maintain a cool feel against the patient's skin, thereby increasing the comfort of the fabric. The fabric 132 can also include additional layers that provide elasticity for maintaining a shape of the fabric as well as to maintain a contacting pressure against the patient's skin.

As further shown in FIG. 1C, the textile digital sensing electrode 130 can include a contact surface 134 configured similar to skin-contacting portion 104 as described above. The contact surface 134 can be configured to couple to the patient's skin. In certain implementations, the contact surface 134 can include a conductive ink that is painted, printed, dyed, or otherwise applied to the fabric 132. For example, the conductive ink can include conductive nanoparticles engineered to have free-standing conductive structures, thereby increasing the effective surface area of the textile digital sensing electrode 130. In other examples, the contact surface 134 can include a pattern of wires and/or conductive threads that are woven or otherwise attached to the fabric 132 so as to not compromise the flexibility of the fabric.

As further shown in FIG. 1C, the textile digital sensing electrode 130 can include a conductive thread or wire 136 that is configured to operably connect the contact surface 134 to additional circuitry components that may not be able to be easily integrated into a flexible electrode such as the textile digital sensing electrode 130. For example, various components as described in relation to PCB 110 above can be positioned at a remote location from the textile digital sensing electrode 130 and operably coupled to the contact surface 134 using wire 136. In certain implementations, the PCB 110, or components of the PCB 110, can be integrated into one or more layers of the garment. In such an example, the garment can function as the housing for the PCB components. In certain implementations, the PCB components can be sown into or otherwise adhered to the garment near the textile digital sensing electrode 130 as shown in FIG. 1C, or at a remote location and be operably coupled to the electrode using, for example wire 136.

Figure 2:
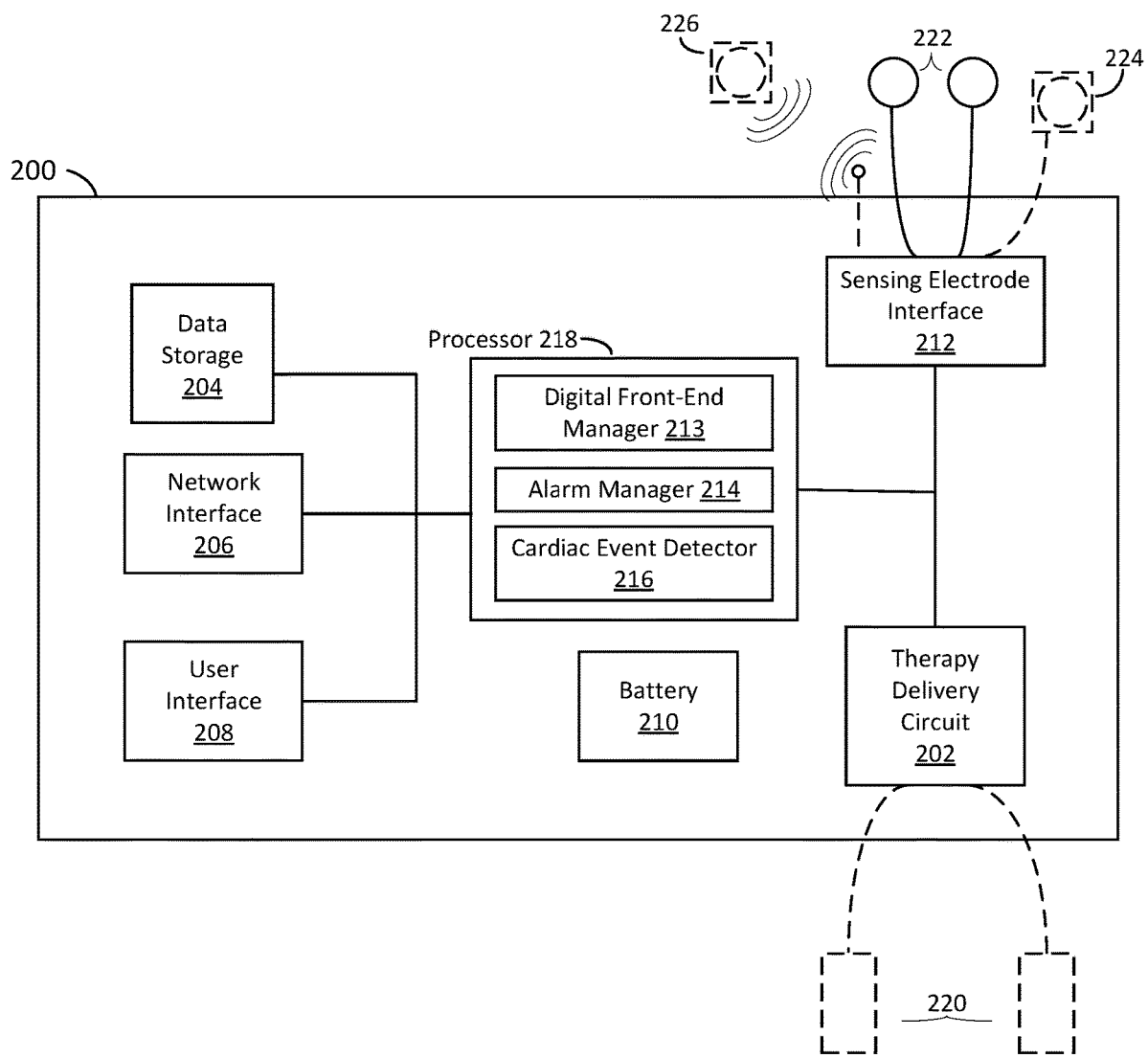
FIG. 2 depicts a schematic view of a sample controller for an ambulatory medical device that includes digital sensing electrodes, in accordance with an example of the present disclosure.

FIG. 2 illustrates an example component-level view of a medical device controller 200 that can be, in some examples, operably connected to one or more digital sensing electrodes such as digital sensing electrode 100 as described above. As shown in FIG. 2, the medical device controller 200 can include a therapy delivery circuitry 202, a data storage 204, a network interface 206, a user interface 208, at least one battery 210, a sensor interface 212, a digital front-end manager 213, an alarm manager 214, a cardiac event detector 216, and least one processor 218.

In some examples, the patient monitoring medical device can include a medical device controller 200 that includes like components as those described above but does not include the therapy delivery circuitry 202 (shown in dotted lines).

The therapy delivery circuitry 202 can be coupled to one or more electrodes 220 configured to provide therapy to the patient. For example, the therapy delivery circuitry 202 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 218) to provide, for example, at least one therapeutic shock to the patient including one or more pacing or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 202 can be configured to perform the switching and pulse delivery operations, e.g., under control of the processor 218. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 200. In certain examples, the data storage can include executable instructions that, when executed, are configured to cause the processor 218 to perform one or more operations.

In some examples, the network interface 206 can facilitate the communication of information between the medical device controller 200 and one or more other devices or entities over a communications network. For example, where the medical device controller 200 is included in an ambulatory medical device, the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 200. The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain examples, the user interface 208 can include one or more physical interface devices such as input devices, output devices, and combination input/output devices and a software stack configured to drive operation of the devices. These user interface elements can render visual, audio, and/or tactile content. Thus, the user interface 208 can receive input or provide output, thereby enabling a user to interact with the medical device controller 200.

The medical device controller 200 can also include at least one battery 210 configured to provide power to one or more components integrated in the medical device controller 200. The battery 210 can include a rechargeable multi-cell battery pack. In one example implementation, the battery 210 can include three or more 2200 mAh lithium ion cells that provide electrical power to the other device components within the medical device controller 200. For example, the battery 210 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 200.

The sensor interface 212 can include physiological signal circuitry that is coupled to one or more sensors configured to monitor one or more physiological parameters of the patient. As shown, the sensors can be coupled to the medical device controller 200 via a wired or wireless connection. The sensors can include one or more digital sensing electrodes 222 (e.g., digital sensing electrodes as described above in connection with FIGS. 1A and 1B), vibration sensor 224, and tissue fluid monitors 226 (e.g., based on ultra-wide band radiofrequency devices). In some implementations, the sensors can include a plurality of conventional ECG sensing electrodes in addition to digital sensing electrodes.

The sensor interface 212 can be coupled to any one or combination of digital sensing electrodes/other sensors to receive other patient data indicative of patient parameters. Once data from the sensors has been received by the sensor interface 212 (e.g., once the sensor interface 212 has received one or more electrode-specific digital signals), the data can be passed to the digital front-end manager 213. In certain implementations, the digital front-end manager 213 can operate in concert with, for example, the processor 218 to perform various non-cardiac event related functions such as noise detection and processing, bio-impedance signal processing, falloff detection, and other operations described in relation to the digital sensing electrodes and/or the electrode-specific digital signals as described herein. In some examples, the functions performed by the digital front-end manager 213 can be performed by the processor 218 or by another component included in the medical device controller 200 as directed by the processor 218.

The digital front-end manager 213 can be implemented using hardware or a combination of hardware and software. For instance, in some examples, the digital front-end manager can be implemented as a software component that is stored within the data storage 204 and executed by the processor 218. In this example, a set of instructions included in the digital front-end manager can cause the processor 218 to perform various processing functions on the electrode-specific digital signals as described herein including, for example, noise detection and processing, bio-impedance signal processing, falloff detection, and other operations as described herein. In other examples, the digital front-end manager 213 can be an application-specific integrated circuit (ASIC) that is coupled to the processor 218. Thus, examples of the digital front-end manager 213 are not limited to a particular hardware or software implementation.

The digital sensing electrodes 222 can monitor a patient's ECG information. For example, by design, the digital sensing electrodes 222 can include skin-contacting electrode surfaces that may be deemed polarizable or non-polarizable depending on a variety of factors including the metals and/or coatings used in constructing the electrode surface. All such electrodes can be used with the principles, techniques, devices and systems described herein. For example, the electrode surfaces can be based on stainless steel, noble metals such as platinum, or Ag—AgCl.

In some examples, the electrodes 222 can be used with an electrolytic gel dispersed between the electrode surface and the patient's skin. In certain implementations, the electrodes 222 can be dry electrodes that do not need an electrolytic material. As an example, such a dry electrode can be based on tantalum metal and having a tantalum pentoxide coating as is described above. Such dry electrodes can be more comfortable for long term monitoring applications.

Referring back to FIG. 2, the digital sensing electrodes 222 can transmit an electrode-specific digital signal descriptive of the analog physiological signals as measured by the individual digital sensing electrodes to the sensor interface 212 for subsequent analysis. For example, the sensor interface 212 can process an electrode-specific digital signal received from the digital sensing electrodes 222 to produce a physiological metric for the patient. In some implementations, the sensor interface, in combination with the processor 218, can perform additional processing and analysis of the electrode-specific digital signals received from the digital sensing electrodes 222 as described below in additional detail.

In certain implementations, the vibration sensors 224 be configured to detect cardiac or pulmonary vibration information. For example, the vibration sensors 224 can detect a patient's heart valve vibration information. For example, the vibration sensors 224 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), percentage of EMAT (% EMAT), systolic dysfunction index (SDI), and left ventricular systolic time (LVST). The vibration sensors 224 can also be configured to detect heart wall motion, for instance, by placement of the sensor in the region of the apical beat. The vibration sensors 224 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 224 can also include a multi-channel accelerometer, for example, a three-channel accelerometer configured to sense movement in each of three orthogonal axes such that patient movement/body position can be detected and correlated to detected cardio-vibrations information. The vibration sensors 224 can transmit information descriptive of the cardio-vibrations information to the sensor interface 212 for subsequent analysis.

The tissue fluid monitors 226 can use radio frequency (RF) based techniques to assess fluid levels and accumulation in a patient's body tissue. For example, the tissue fluid monitors 226 can be configured to measure fluid content in the lungs, typically for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

In some examples, the sensor interface and/or the digital front-end manager 213 can work in concert with the processor 218 to direct at least a portion of, for example, an electrode-specific digital signal to an appropriate component within the medical device controller 200. For example, if heart data is collected by vibration sensor 224 and transmitted to the sensor interface 212, the sensor interface 212 can transmit the data to the processor 218 which, in turn, relays the data to the cardiac event detector 216. The cardiac event data can also be stored on the data storage 204.

In certain implementations, the alarm manager 214 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 218. In this example, the instructions included in the alarm manager 214 can cause the processor 218 to configure alarm profiles and notify intended recipients using the alarm profiles. In other examples, alarm manager 214 can be an application-specific integrated circuit (ASIC) that is coupled to the processor 218 and configured to manage alarm profiles and notify intended recipients using alarms specified within the alarm profiles. Thus, examples of alarm manager 214 are not limited to a particular hardware or software implementation.

In certain implementations, the cardiac event detector 216 can be configured to monitor a patient's ECG signal for an occurrence of a cardiac event such as an arrhythmia or other similar cardiac event. The cardiac event detector can be configured to operate in concert with the processor 218 to execute one or more algorithms to process received ECG signals from, for example, the digital sensing electrodes 222 and determine the likelihood that a patient is experiencing a cardiac event. If the patient is experiencing a cardiac event, the cardiac event detector can provide information to the alarm manager 214 to follow one or more alarm profiles related to the determined cardiac event. The cardiac event detector 216 can be implemented using hardware or a combination of hardware and software. For instance, in some examples, cardiac event detector 216 can be implemented as a software component that is stored within the data storage 204 and executed by the processor 218. In this example, the instructions included in the cardiac event detector 216 can cause the processor 218 to perform one or more algorithms for analyzing a received ECG signal to determine whether an adverse cardiac event is occurring. In other examples, the cardiac event detector 216 can be an application-specific integrated circuit (ASIC) that is coupled to the processor 218 and configured to monitor ECG signals for adverse cardiac event occurrences. Thus, examples of the cardiac event detector 216 are not limited to a particular hardware or software implementation.

In some implementations, the processor 218 includes one or more processors (or one or more processor cores) that each are configured to perform a series of instructions that result in manipulated data and/or control the operation of the other components of the medical device controller 200. In some implementations, when executing a specific process (e.g., cardiac monitoring), the processor 218 can be configured to make specific logic-based determinations based on input data received, and be further configured to provide one or more outputs that can be used to control or otherwise inform subsequent processing to be carried out by the processor 218 and/or other processors or circuitry with which processor 218 is communicatively coupled. Thus, the processor 218 reacts to specific input stimulus in a specific way and generates a corresponding output based on that input stimulus. In some example cases, the processor 218 can proceed through a sequence of logical transitions in which various internal register states and/or other bit cell states internal or external to the processor 218 can be set to logic high or logic low. As referred to herein, the processor 218 can be configured to execute a function where software is stored in a data store coupled to the processor 218, the software being configured to cause the processor 218 to proceed through a sequence of various logic decisions that result in the function being executed. The various components that are described herein as being executable by the processor 218 can be implemented in various forms of specialized hardware, software, or a combination thereof. For example, the processor 218 can be a digital signal processor (DSP) such as a 24-bit DSP. The processor 218 can be a multi-core processor, e.g., having two or more processing cores. The processor 218 can be an Advanced RISC Machine (ARM) processor such as a 32-bit ARM processor or a 64-bit ARM processor. The processor 218 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more megaohms). This high source impedance signal is processed and transmitted to a monitoring device such as processor 218 of the controller 200 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 3A:
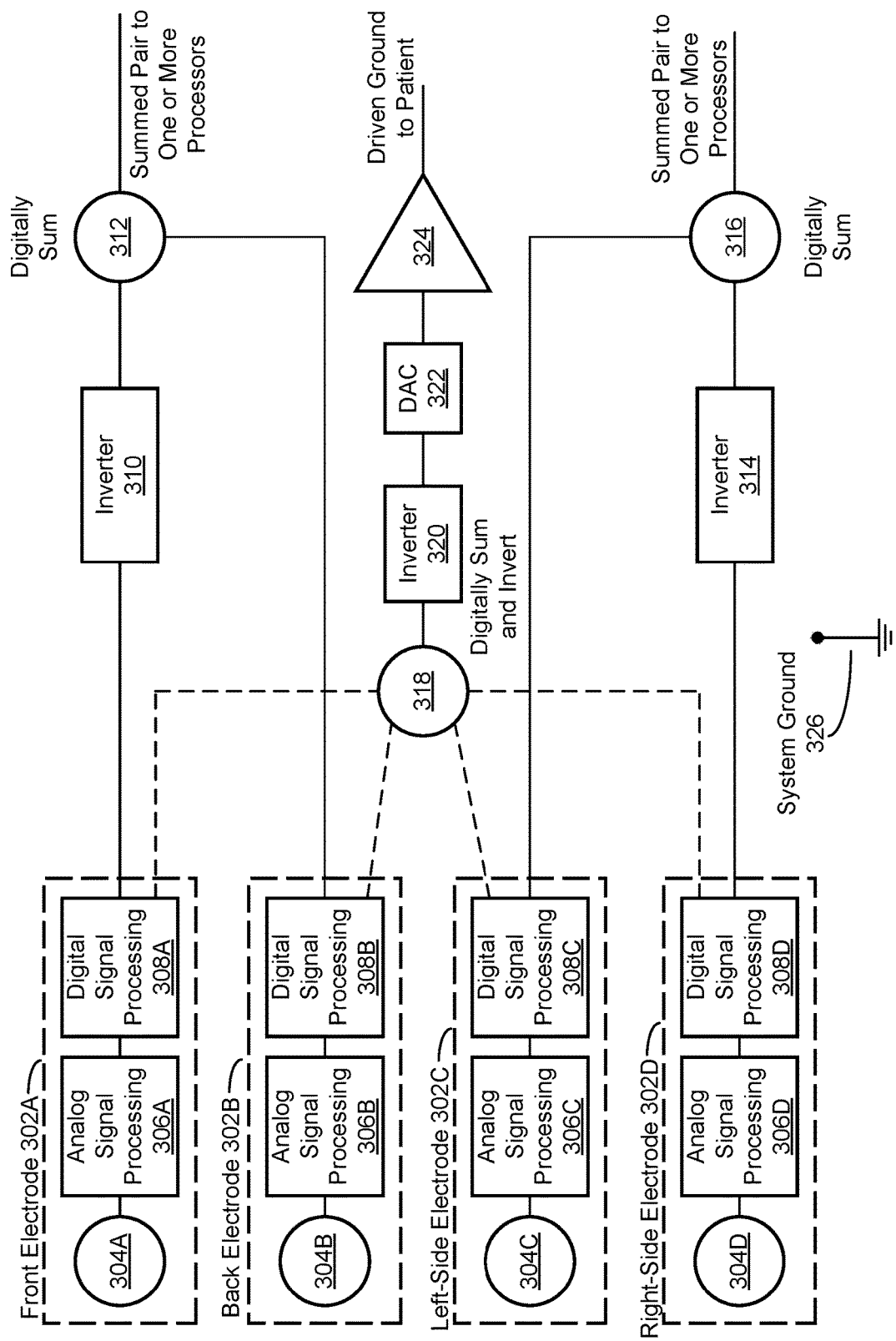
FIGS. 3A and 3B depict sample implementation diagrams for digital electrodes in an ambulatory medical device, in accordance with an example of the present disclosure.

FIG. 3A illustrates an example implementation view of a digital front-end approach using digital sensing electrodes as described herein. For example, as shown in FIG. 3A, the ambulatory medical device can include four digital sensing electrodes, front electrode 302A, back electrode 302B, left-side electrode 302C, and right-side electrode 302D. In certain implementations, each of the digital sensing electrodes 302A-302D can include additional circuitry components. For example, each digital sensing electrode can include a skin-contacting portion (e.g., a tantalum pentoxide disk) configured to contact the patient's skin. Each digital sensing electrode can also include processing circuitry configured to, for example, perform additional processing such as signal buffering, amplification, conditioning, and analog-to-digital signal conversion.

Thus, as shown in FIG. 3A, front electrode 302A includes skin-contacting portion 304A, analog signal processing circuitry 306A, and digital signal processing circuitry 308A. Similarly, the back electrode 302B includes skin-contacting portion 304B, analog signal processing circuitry 306B, and digital signal processing circuitry 308B. As further shown in FIG. 3A, the left-side electrode 302C includes skin-contacting portion 304C, analog signal processing circuitry 306C, and digital signal processing circuitry 308C. Similarly, the right-side electrode 302D includes skin-contacting portion 304D, analog signal processing circuitry 306D, and digital signal processing circuitry 308D.

The outputs of each of the digital sensing electrodes can be further processed at, for example, a belt node integrated into the ambulatory medical device or at the device controller such as medical device controller 200 as described above. For example, as shown in FIG. 3A, during the additional processing, the output of the front electrode 302A can be inverted by inverter 310 and summed with the output of the back electrode 302B by digital summing circuit 312. Similarly, as further shown in FIG. 3A, the output of the right-side electrode 302D can be inverted by inverter 314 and summed with the output of the left-side electrode 302C by digital summing circuit 316. Each of the summed pairs (i.e., front-back pair and left-side-right-side pair as shown in FIG. 3A) can be transmitted or otherwise output to one or more processors for additional processing. For example, the summed pairs can be analyzed to determine one or more ECG metrics for the patient.

In FIG. 3A, the output of front digital sensing electrode 302A and the output of right-side digital sensing electrode 302D are shown as being inverted prior to being digitally summed with the output of back digital sensing electrode 302B and left-side digital sensing electrode 302C respectively. This is shown by way of example only and, depending upon the arrangement of the digital sensing electrodes and the ECG plane the electrode pairs are positioned on, the outputs of digital sensing electrodes other than the front and right-side electrodes 302A and 302D can be inverted prior to the digital summing. In certain implementations, the outputs of the digital sensing electrodes 302A-302D can be inverted by, for example, the digital signal processing circuitry 308A-308D respectively. For example, one or more of the digital signal processing circuitry 308A-308D can receive a configuration message from the device controller to invert their output.

Additionally, as further shown in FIG. 3A, the outputs of each of the digital sensing electrodes 302A-302D can be digitally summed by digital summing circuit 318 to produce a summed common noise signal. This summed common noise signal can be inverted by inverter 320 and converted to an analog signal by digital-to-analog converter (DAC) 322. In certain implementations, the output of the DAC 322 can be input into a buffer amplifier 324 and provided to the patient as a driven ground signal using, for example, a driven right leg circuit as described above. In certain implementations, the buffer amplifier 324 can be configured as a low impedance source driving a virtual ground reference that provides a low impedance path to ground (e.g., between about 10 to 100 ohms) having little voltage potential between the patient and a system/analog ground. In some examples, this driven ground can be a portion of a reference voltage used to provide a common reference value across multiple components in the system. For example, and as described in greater detail below in reference to FIGS. 4A and 4B, the buffer amplifier can be configured to output a driven ground that is approximately half the voltage of a system reference voltage as referenced to, for example, a system ground 326 as shown in FIG. 3A. For example, the system ground 326 can be configured to provide a baseline voltage to reference or otherwise bias a system voltage to. In some examples, the system ground 326 can be configured to provide a reference of zero volts. In other examples, the system ground 326 can be configured to provide a low voltage that is about zero volts (e.g., between about 5 millivolts and about 25 millivolts).

In a certain implementation, the system voltage can be 5 volts as referenced to the system ground 326. In such an example, the output voltage of the driven ground will be 2.5 volts (½ the reference voltage of 5 volts). However, it should be noted that 5 volts is provided as the reference voltage by way of example only and other voltages can be used for the reference voltage. For example, in some implementations the reference voltage can be selected from the range of about 2.5 volts to about 7.5 volts. In other implementations, the reference voltage can be selected from the range of about 0.5 volts to about 12 volts.

As noted above in reference to FIG. 3A, the digital sensing electrodes can be arranged into pairs such as front-back and side-side for further processing. However, this is shown by way of example only as a sample implementation. As described herein below, by converting the outputs of the digital sensing electrodes to digital signals, the digital sensing electrodes can be dynamically paired based upon the output of each of the digital sensing electrodes. For example, an ambulatory medical device controller such as medical device controller 200 as described above can include a default setting configured to monitor the patient using front-back and side-side pairings. Upon detecting noise or another similar interference that impacts signal quality on one or more of the digital sensing electrodes, the medical device controller can dynamically change the pairings to improve the monitoring performance of the ambulatory medical device. For example, the medical device controller can pair the digital sensing electrodes such that the front digital sensing electrode is paired with the left-side digital sensing electrode, and the back digital sensing electrode is paired with the right-side digital sensing electrode.

Figure 3B:
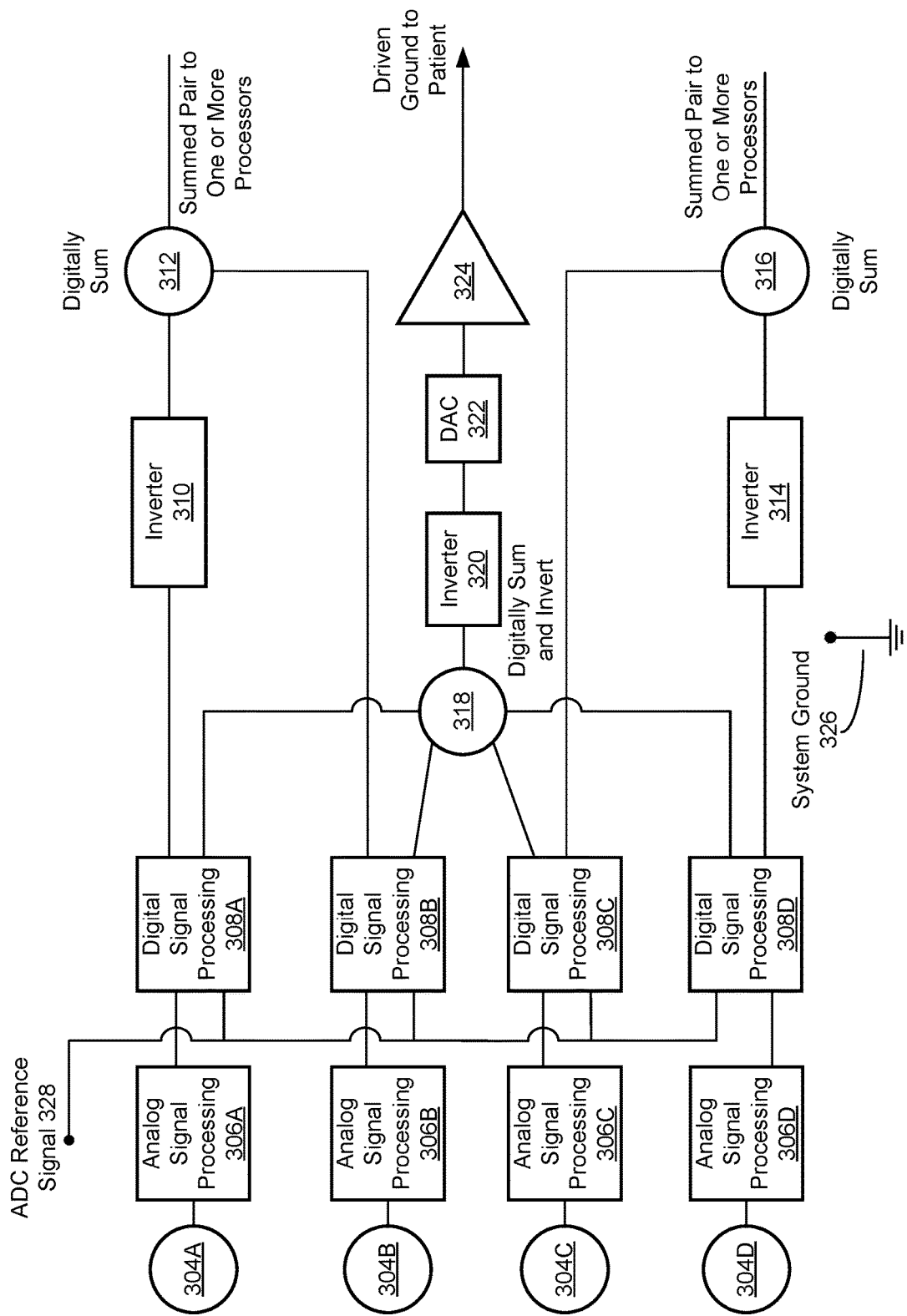

FIG. 3B illustrates an additional example implementation view of a digital front-end approach using digital sensing electrodes as described herein. Similar to the overview as shown in FIG. 3A, the implementation as shown in FIG. 3B includes an additional ADC reference signal 328 being provided as an additional input for further processing at each of the sensing electrodes.

For example, the reference signal 328 can include a system voltage that is referenced to the system ground 326 so that it provides a fixed system voltage for each of the digital sensing electrodes to use, thereby providing a common operational voltage to each of the digital sensing electrodes. In some examples, the reference signal can also include system ground 326 such that the digital signal processing circuitry components in each of the digital sensing electrodes have a common ground reference. Reference signal 328 is shown as being an input for the digital signal processing circuitry 308A-308D by way of example only. In certain implementations, the reference signal 328 can be provided to various other components of the digital sensing electrodes 302A-302D such as the analog signal processing components 306A-306D as well.

As further described below in regard to FIGS. 4A and 4B, each of the digital sensing electrodes 302A-302D can include an integrated circuit configured to use the provided system voltage and system ground 326 to generate a reference voltage similar to (or, in some examples, identical to) the reference voltage as described above in the driven ground discussion. In certain implementations, the reference signal 328 can also include a synchronization signal for the ADCs to synchronize their operation, calibration data, configuration data, and other information for the programming and/or operation of the digital sensing electrodes.

Figure 4A:
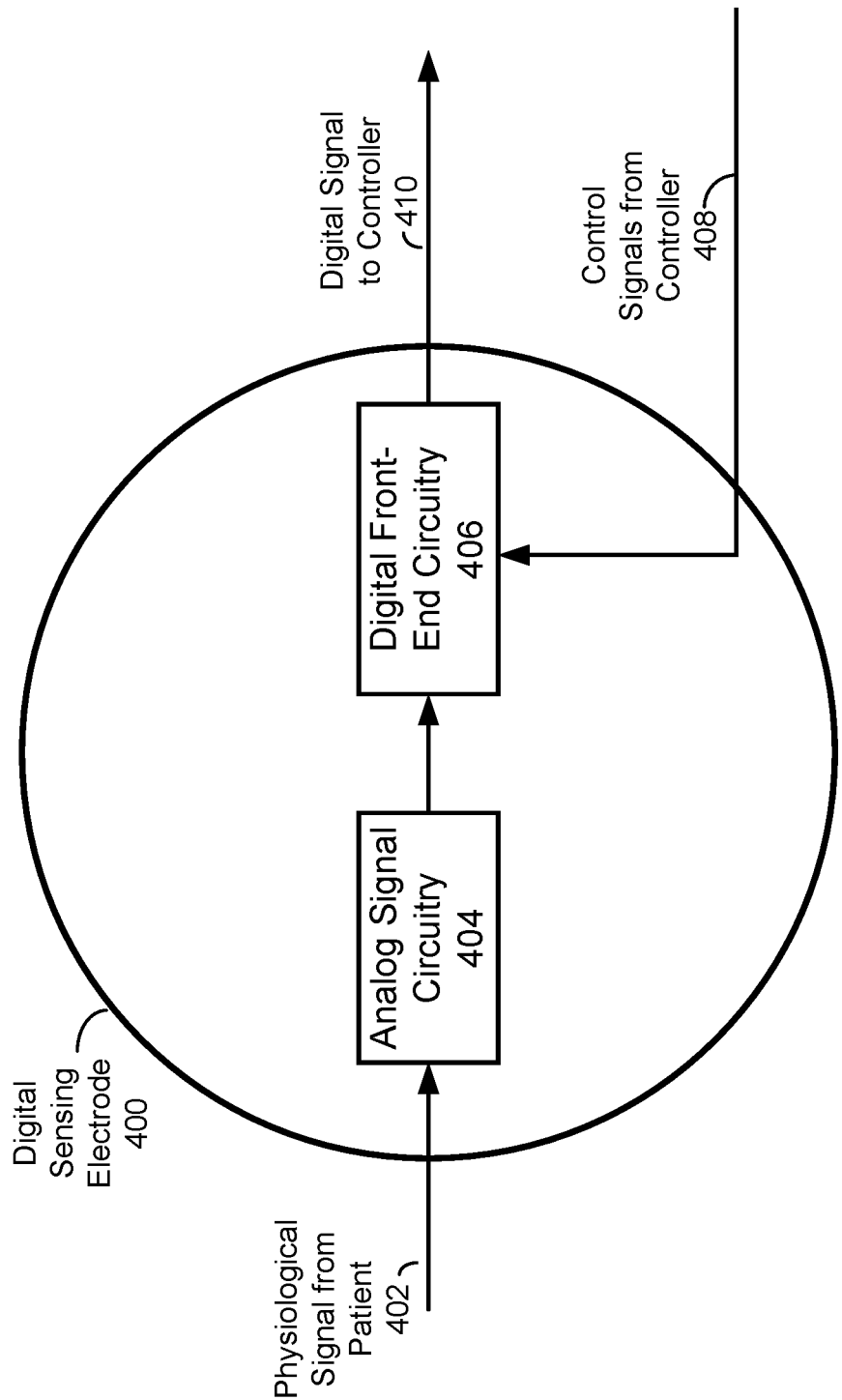
FIG. 4A depicts a sample circuit diagram of a digital sensing electrode for use with an ambulatory medical device, in accordance with an example of the present disclosure.

FIG. 4A depicts a sample circuitry diagram for a digital sensing electrode incorporated into a digital front-end of an ambulatory medical device as described herein. For example, as shown in FIG. 4A, the digital sensing electrode 400 can receive a physiological signal 402 from the patient's body. As noted above, this physiological signal 402 can be measured or otherwise detected by a skin-contacting portion of the digital sensing electrode that is in contact with the patient's skin. For example, the physiological signal 402 can include electrical signals detected by a tantalum pentoxide disk in contact with the patient's skin. Similar to the implementations as shown in FIGS. 3A and 3B, and described above in reference to these figures, the physiological signal 402 can be input to analog signal circuitry 404. In certain implementations, the analog signal circuitry can be configured to process and condition the physiological signal 402 for further processing. The output of the analog signal circuitry can be input to digital front-end circuitry 406 for additional signal processing such as conversion from a conditioned analog signal to a digital signal. The digital front-end circuitry 406 can be operably connected to a controller (e.g., controller 200 as described above) to receive one or more control signals 408 from the controller. These control signals 408 can include, for example, similar signals as described in regard to the reference signal 328 described above. The output of the digital front-end circuitry 406 can be transmitted or otherwise output as an electrode-specific digital signal 410 and directed to the controller.

In certain implementations, the analog signal circuitry 404 and the digital front-end circuitry 406 can include various circuitry related to operation and functionality of the digital sensing electrode 400 arranged and integrated into a PCB such as PCB 110 as described above. As shown in FIG. 4B, the digital sensing electrode 400 can include additional components not shown in FIG. 4A. For example, the digital sensing electrode can include an integrated power circuit 412. In certain implementations, the power circuit 412 can receive a system voltage (included, for example, in the control signals 408 received form the device controller) and generate one or more output voltages as referenced or biased to, for example, system ground 326. For example, the power circuitry 412 can output a reference voltage $V_{Ref}$ and a portion or fraction of the reference voltage, in this example, half the reference voltage ½ $V_{Ref}$. As noted above, in certain examples $V_{Ref}$ can be approximately 5 volts as referenced to the system ground 326, and ½ $V_{Ref}$ can be approximately 2.5 volts. Each digital sensing electrode (e.g. digital sensing electrodes 302A, 302B, 302C, and 302D as described herein) can include a similarly calibrated and rated power circuit 412 such that the $V_{Ref}$ (and ½ $V_{Ref}$) produced at each digital sensing electrode is identical or, in some implementations, approaching a<=0.01% tolerance.

Figure 4B:
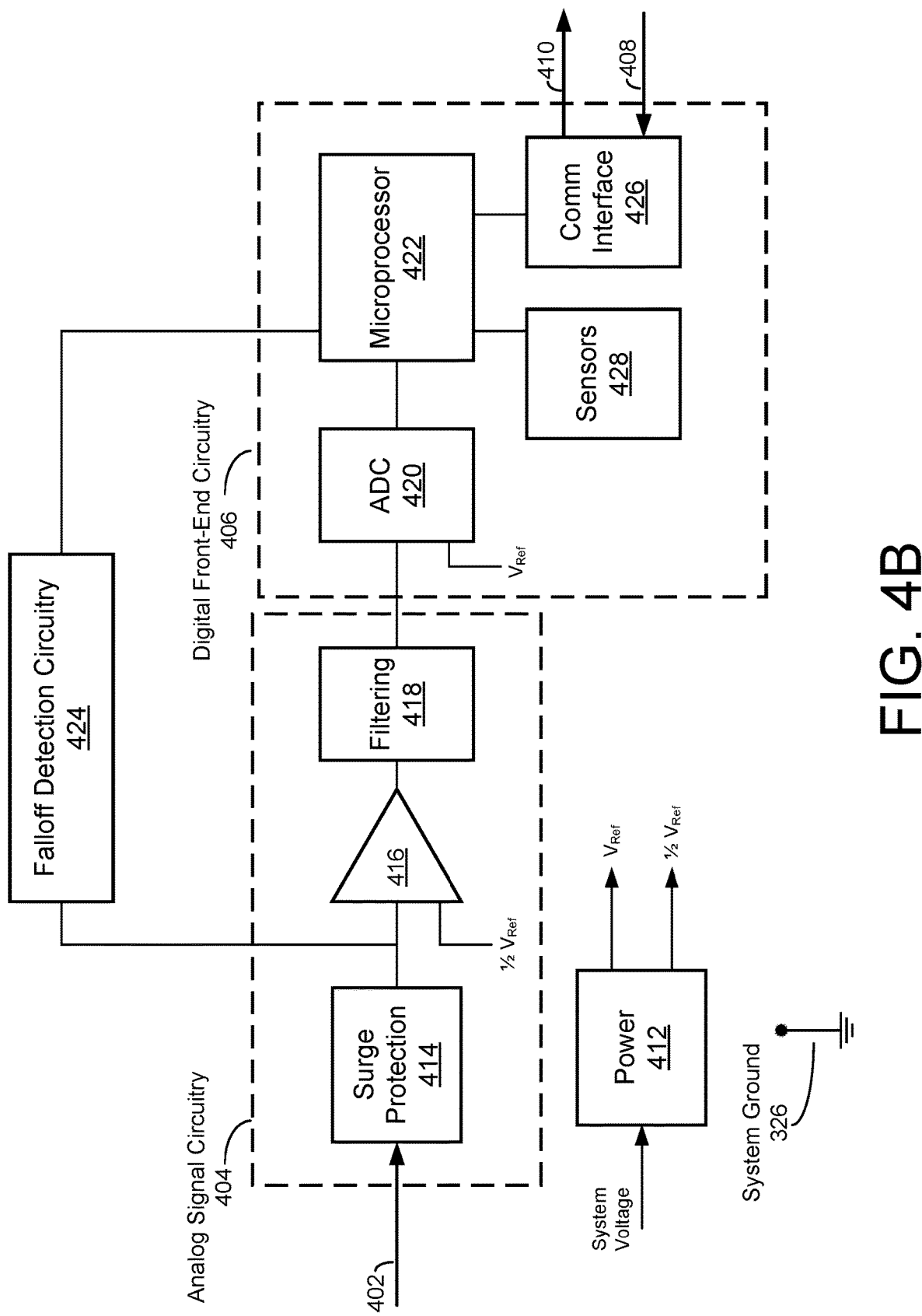
FIG. 4B depicts a sample circuit diagram of electrode circuitry to be included in a digital sensing electrode such as that illustrated in FIG. 4A, in accordance with an example of the present disclosure.

As further shown in FIG. 4B, and described above in reference to FIG. 4A, the physiological signal 402 from the patient can be input to the analog signal circuitry 404. In certain implementations, the physiological signal 402 can be passed through protection circuitry such as surge protection circuit 414 before being further processed. The surge protection circuit 414 can be configured to prevent unwanted current from traveling through, for example, the analog signal circuitry 404 and the digital front-end circuitry 406. For example, if the digital sensing electrode 400 is integrated into an ambulatory medical device that includes therapy electrodes for providing an electrical shock to the patient, the surge protection circuitry 414 can be configured to protect the digital sensing electrode to prevent any portion of the treatment shock being directed to the controller or to any internal circuitry components of the digital sensing electrode itself.

The output of the surge protection circuit 414 can be input into a buffer amplifier 416 with relatively high impedance (e.g., about 100 megaohms or more) to accommodate a high source impedance that is typically associated with, for example, bio-potential measurements made with polarizable sensors. The low output impedance of the buffer amplifier 416 is conditioned to drive the relatively low impedance circuit (e.g., about 10 to 100 ohms) of the remaining components of the digital front-end circuitry 406. As shown in FIG. 4B, the buffer amplifier 416 can be configured as a voltage buffer and use ½ $V_{Ref}$ (as output by the power circuit 412) as the voltage source. The output of buffer amplifier 416 can be filtered by filtering circuit 418 to perform additional processing such as signal enhancement or removal of unwanted frequency components. The filtered and otherwise conditioned analog signal can be output from the analog signal circuitry 404 and input to the digital front-end circuitry 406. Other analog input circuitry architectures can be used. For example, a composite amplifier structure configured to yield a high input impedance while providing requisite amplification and filtering can be included. Such a structure can be configured to minimize non-ideal circuit behavior such as input-offset amplification, noise, and input bias effects.

As shown in FIG. 4B, the conditioned analog signal can be input to an ADC 420 for conversion from an analog signal to a digital signal. In certain implementations such as that shown in FIG. 4B, the ADC 420 can have an input voltage equal to $V_{Ref}$ as described above and generated by power circuit 412. As each digital sensing electrode 400 in the system includes a similarly configured and calibrated power circuit 412, and each digital sensing electrode shares system ground 326, the identical (or nearly identical) $V_{Ref}$ as generated and input to the ADCs results in each ADC (at each digital sensing electrode) having an identical reference voltage and voltage bias as referenced to the system ground 326. As such, the resulting digital signals as produced by the ADC 420 for each digital sensing electrode will be similarly scaled and biased for further processing by the controller.

In certain implementations, the ADC 420 can be a successive approximation ADC. A successive approximation ADC is a type of converter that uses a successive approximation register (SAR) to convert a continuous analog waveform into a discrete digital representation via a binary search through all possible quantization levels before finally converging upon a digital output for each conversion. In certain implementations, the ADC 420 can be dynamically adjustable to alter a sampling rate of the conversion. For example, the ADC 420 can be adjusted to sample at rates from about 50 samples per second to about 1 million samples per second (1 mega-samples/sec). In some examples, the digitized signal as produced by the ADC 420 can be decimated or downsampled. For example, the ADC 420 can be set to sample at a rate of 2000 samples per second and decimated to 400 samples per second by a processor at, for example, the medical device controller. By sampling the signal at a higher rate and then decimating sampled signal, the signal to noise ratio of the signal can be increased (as compared to a non-decimated signal) which can improve signal resolution. In certain implementations, the ADC 420 can be configured to change sampling rates dynamically in response to, for example, a signal from the device controller to increase or decrease its sampling rate. For example, if the signal to noise ratio for a particular digital sensing electrode decreases, the device controller can send an instruction to the ADC 420 integrated into that ADC to increase its sampling rate and apply decimation.

As further shown in FIG. 4B, the digital front-end circuitry 406 can include a microprocessor 422 operably coupled to ADC 420. The microprocessor 422 can be configured to function as an information gateway between, for example, the digital sensing electrode 400 and the device controller. In certain implementations, the microprocessor 422 can be operably coupled to a communications interface 426 that is configured to convert the output of the microprocessor according to a communications protocol used to communicate with the controller. For example, the control can be configured to communicate using the RS485 protocol. The communications interface 426 can be configured to receive information from the microprocessor 422 and convert the information to an appropriate format for transmission to and processing by the controller. Conversely, the communications interface 426 can be configured to receive information from the controller (e.g., the controls signals 408) and convert the information to an appropriate format for processing by the microprocessor 422. It should be noted, however, that the microprocessor 422 as shown in FIG. 4B is provided by way of example only. In certain implementations, additional processors such as a 24-bit DSP, a multi-core processor, a 32-bit or a 64-bit ARM processor, or another similar processor configured to execute one or more instructions to provide a service or related functionality. In some examples, the digital electrode 400 can be configured to operate without a microprocessor 422. For example, a series of control lines can be configured to carry output signals directly from the digital sensing electrode to a centralized processor that is configured to perform the functionality of the microprocessor 422.

In certain implementations, the digital front-end circuitry 406 can further include additional sensors 428 operably coupled, for example, to the microprocessor 422. In some examples, the additional sensors 428 can include motion sensors such as three-axis accelerometers, (as described below in additional detail in reference to FIG. 8A), temperature sensors, humidity sensors, acoustic sensors, and other similar sensors. However, it should be noted that the sensors 428 are shown as included in the digital front-end circuitry 406 by way of example only. In certain implementations, the sensors 428 can be positioned or otherwise integrated into other portions of the digital electrode 400.

The digital sensing electrode 400 can further include falloff detection circuitry 424 that is configured to identify whether a digital sensing electrode has lost contact with the patient's skin or where the contact with the patient's skin is otherwise compromised resulting in a noisy signal. In certain implementations, electrode-skin contact can be assessed by passing a small excitation signal through the body and measuring the resultant response at one or more digital sensing electrodes. For example, an excitation current source can be applied to the patient's skin at fixed frequency and the response measured locally at one or more digital sensing electrodes such as the digital sensing electrodes as described herein. The falloff detection circuitry 424 can include a local oscillator (LO) that can be phase matched to the excitation source. For example, both the excitation source and the LO can be set to about 800 Hz in order to perform synchronous detection. The LO can cause an amplifier included in the falloff detection circuitry 424 to alternate between inverting and non-inverting to synchronously rectify the received signal. The result can be filtered and compared against, for example, a programmable threshold to assess electrode-skin contact. The result of the comparison can be passed to, for example, the microprocessor 422 for further processing.

The falloff circuitry 424 and the determination of a digital electrode falloff condition is shown as being performed by dedicated falloff circuitry by way of example. Alternatively or in addition, falloff detection can be performed by the microprocessor 422 executing encoded instructions based on, for example, a fast Fourier transform or the Goertzel algorithm.

It should also be noted that the circuitry components associated with the digital sensing electrode 400 as shown in FIG. 4B, and their associated arrangement into, for example, analog signal circuitry 404 and digital front-end circuitry 406, is provided by way of example only. Depending upon the implementation of the digital sensing electrode 400, the components and functionality contained within the circuitry components as shown in FIG. 4B can vary. For example, in certain implementations the $V_{Ref}$ voltage can be provided to each digital sensing electrode in the control signals 408 and, as such, the power circuit 412 can be removed from each digital sensing electrode.

Figure 5A:
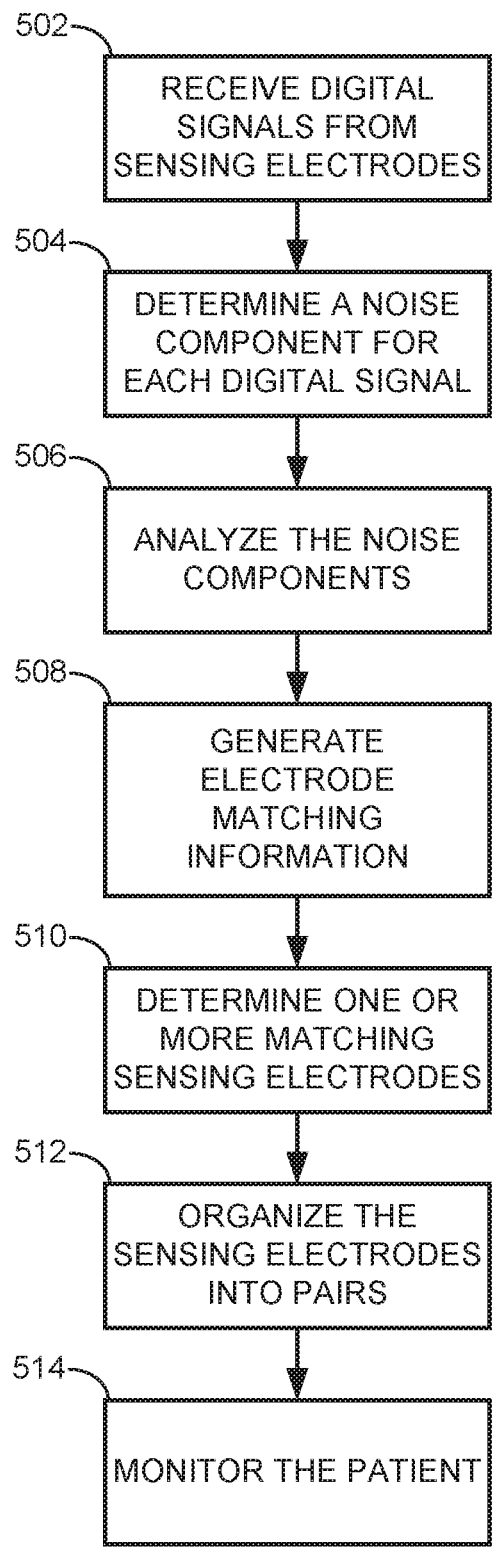
FIG. 5A depicts a sample process flow for matching digital sensing electrodes and determining electrode pairs in an ambulatory medical device, in accordance with an example of the present disclosure.

As noted above, by providing a digital front-end having multiple digital sensing electrodes, a monitoring device such as medical device controller 200 as described above can receive an electrode-specific digital signal from each digital sensing electrode for further processing. For example, FIG. 5A illustrates a sample process flow implemented by, for example, a digital front-end management component such as digital front-end manager 213 of medical device controller 200 as described above. The digital front-end manager can be configured to work in concert with a processor, such as processor 218, to match digital sensing electrodes and dynamically update digital sensing electrode pairs when monitoring a patient. It should be noted that the following description of the process as shown in FIG. 5A is presented as being executed by the processor, but it should be noted that the processor and the digital front-end manager can operated in concert to execute the process as shown in FIG. 5A and described herein.

Referring now to FIG. 5A, the processor can receive 502 an electrode-specific digital signal from each of the digital sensing electrodes. For example, as described above, each digital sensing electrode can be configured to generate and output an electrode-specific digital signal and transmit or otherwise direct the signal to the processor. The processor can determine 504 a noise component for each of the electrode-specific digital signals. For example, the noise component can include any signal component outside of a specific frequency range of interest. The processor can be configured to filter the electrode-specific digital signals to identify, isolate, and attenuate various noise components. For example, the processor can identify noise as changes in measured impedance values for a 60 Hz signal measured by the digital sensing electrodes. Additionally, or alternatively, the processor can measure noise as measured gain or voltage change over a bandwidth of interest. The processor can identify any signals, or portion of signals, outside of the bandwidth of interest as irrelevant or noise. For example, the processor can monitor a signal having a bandwidth of interest of about 0.50 Hz to about 200 Hz. In some implementations, the bandwidth can be between about 0.50 Hz to about 150 Hz. The processor can identify any measured signals outside of such bandwidth of interest as irrelevant or noise. The bandwidth of interest can be set prior to the monitoring phase or be dynamically adjusted during the monitoring, depending on the ECG features being monitored.

Figure 5B:
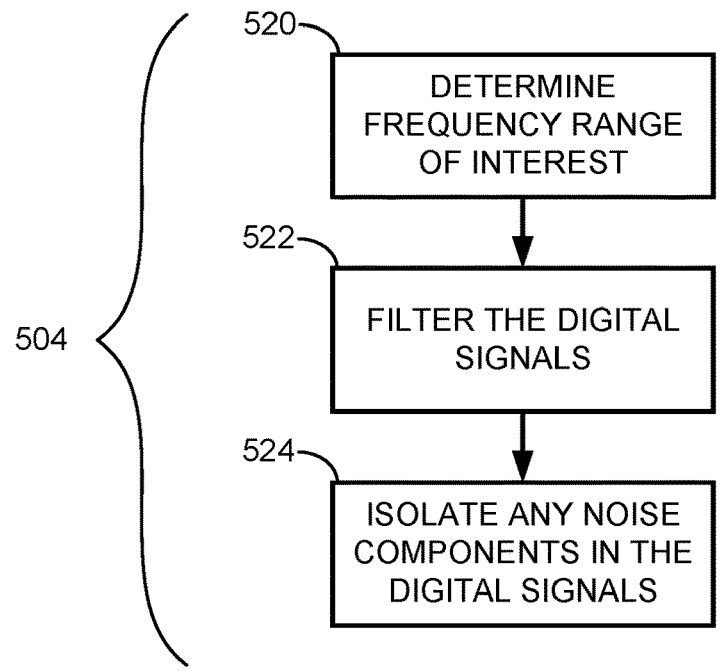
FIGS. 5B and 5C depict sample implementations of one or more process steps as shown in FIG. 5A, in accordance with an example of the present disclosure.

FIG. 5B illustrates a sample process for determining 504 noise components for each of the electrode-specific digital signals. For example, as shown in FIG. 5B, the processor can determine 520 a frequency range of interest. As noted above, the processor can identify noise as changes in measured impedance values for a 60 Hz signal. In such an implementation, the processor can determine 520 a frequency range of interest to be 60 Hz plus or minus 15 Hz. As such, in this example, the processor can determine 520 a frequency range of interest of about 45 Hz to about 75 Hz. In implementations, the frequency range of interest can be different. For example, in certain implementations the frequency range of interest can be narrower, such as 55 Hz to 65 Hz.

As further shown in FIG. 5B, the processor can filter 522 the electrode-specific digital signals to identify any signal components that fall outside of the frequency range of interest. In the above example, the processor can filter 522 the electrode-specific digital signals to identify any signal components that are above 75 Hz or below 45 Hz. The processor can isolate 524 any signal components in the electrode-specific digital signals and label the isolated signal components as noise components for each of the electrode-specific digital signals.

Referring back to FIG. 5A, the processor can further analyze 506 the noise components from each of the electrode-specific digital signals to identify similar noise components or patterns in the noise components between individual digital sensing electrodes. For example, the processor can identify a signal strength value for each of the digital sensing electrodes as well as signal-to-noise ratios for each of the digital sensing electrodes based upon the analyzed noise components.

Figure 5C:
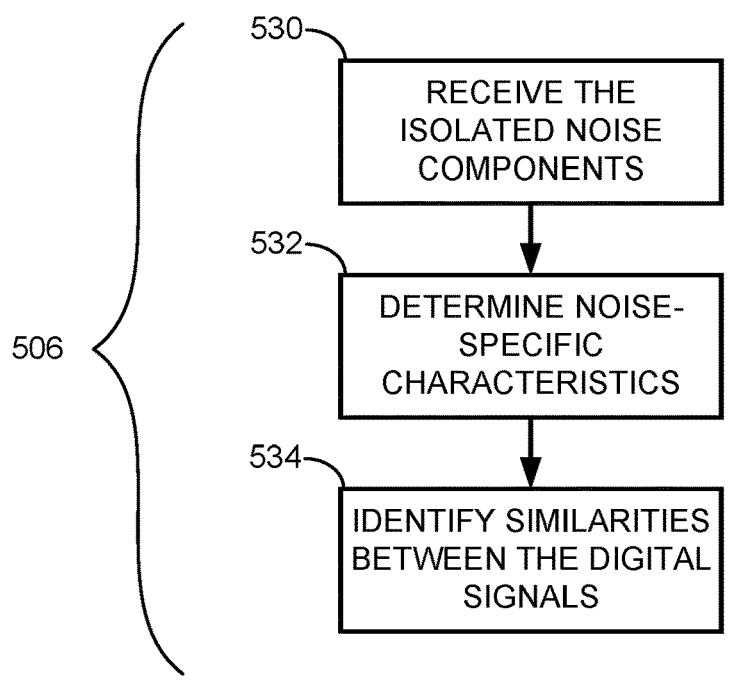

FIG. 5C illustrates a sample process for analyzing 506 the noise components from each of the electrode-specific digital signals. For example, as shown in FIG. 5C, the processor can receive 530 each of the isolated noise components for each electrode-specific digital signal (isolated, for example, as noted above in the discussion of FIG. 5B). The processor can analyze the isolated noise components to determine 532 one or more noise-specific characteristics for each of the electrode-specific digital signals. For example, the processor can determine 532 signal strength information, amount of noise, signal-to-noise ratios, and other similar characteristic information for each of the electrode-specific digital signals. Based upon the noise-specific characteristics, the processor can identify 534 similarities between the electrode-specific signals. For examples, the processor can identify electrode-specific signals with similar signal strengths and/or similar signal-to-noise ratios.

Referring back to FIG. 5A, based upon the signal similarity information as determined above, the processor can generate 508 electrode matching information and determine 510 one or more matching digital sensing electrodes. For example, the processor can be configured to match digital sensing electrodes that have noise components that, when combined, would cancel or partially cancel each other out, thereby providing a cleaner electrode pair signal. Additionally, or alternatively, the processor can be configured to match digital sensing electrodes that have similar signal strengths or similar signal-to-noise ratios. The matching information can be used to rank potential digital electrode pairs based upon likely signal quality when paired. The processor can use the determined matching information, and the electrode rankings, to organize 512 the digital sensing electrodes into pairs and monitor 514 the patient using the digital sensing electrode pairs. The flow as shown in FIG. 5A can be repeated by the processor to provide for the digital sensing electrode pairs to be updated regularly to provide digital sensing electrode pairs that provide the highest quality signals.

In some examples, the processor can be further configured to adjust the individual voltage gain at one or more of the digital sensing electrodes to improve the noise components in the electrode-specific digital signals. For example, the processor can adjust the gain at one or more of the digital sensing electrodes and monitor for changes in the noise components of the electrode-specific digital signals generated by those digital sensing electrodes. Based upon changes in the noise components, the processor can update the digital sensing electrode pairs to reflect the changes in the noise components and potentially improve signal quality for the digital sensing electrode pairs.

Additionally, in some implementations, the processor can be further configured to adjust the digital sensor pairings for other reasons. For example, the processor can adjust the digital sensor pairings to provide an alternative plane or view of the electrical activity of the heart during monitoring. The pairings can be adjusted continually to provide different views of the heart activity during different portions of a cardiac cycle. Additionally, the pairings can be updated to provide additional information such as additional T-wave information obtained from collecting multiple views of the heart through different digital sensing electrode pairings. A similar process as that described in FIGS. 5A-5C can be used to determine which digital sensor pairings will provide updated views of a patient's cardiac activity.

Figure 6A:
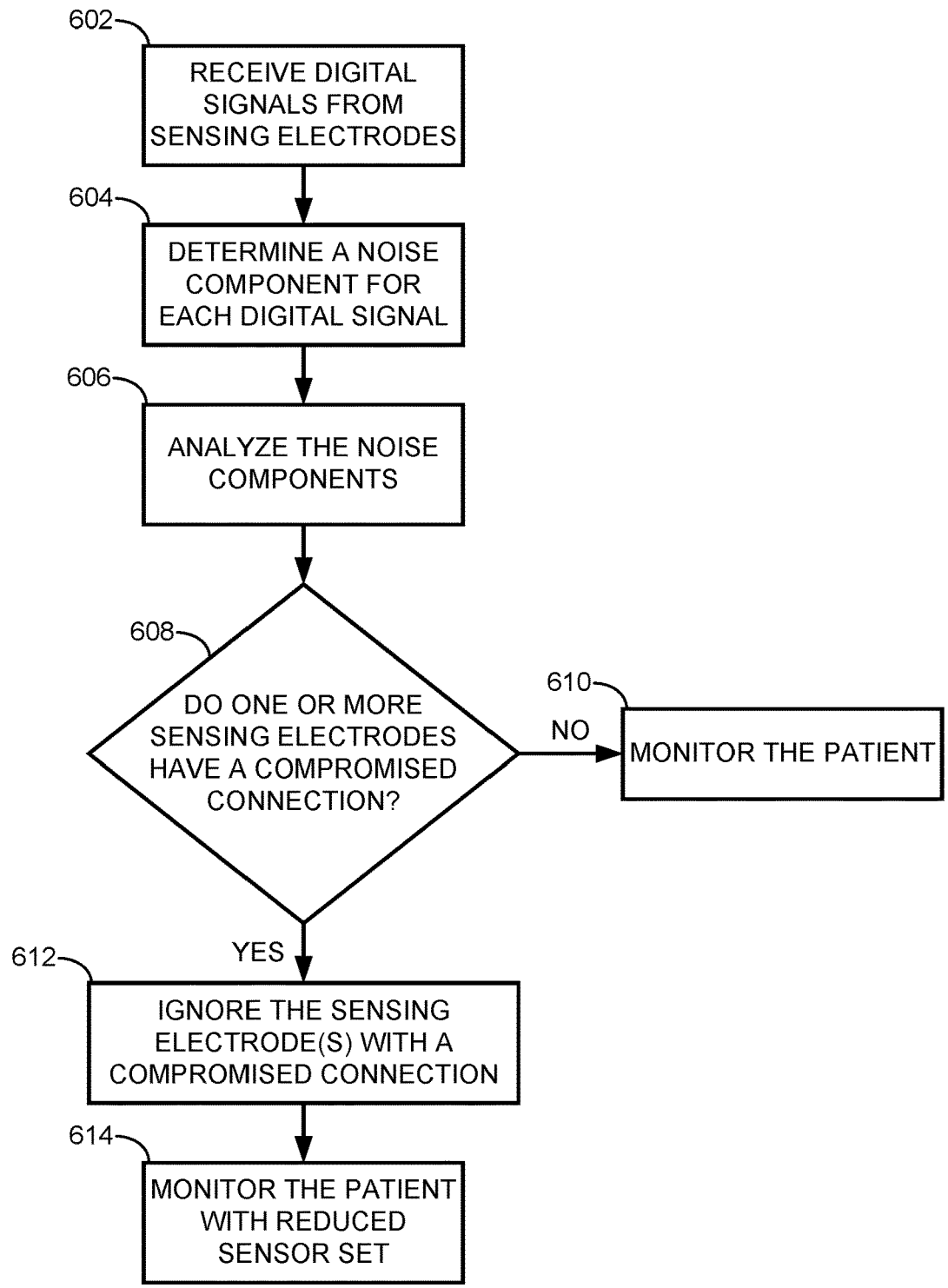
FIG. 6A depicts a sample process flow for determining whether a digital sensing electrode has a compromised connection with the patient, in accordance with an example of the present disclosure.

FIG. 6A illustrates a sample process flow implemented by, for example, a digital front-end management component such as digital front-end manager 213 of medical device controller 200 as described above. The digital front-end manager can be configured to work in concert with a processor such as processor 218 as described above or a dedicated processor such as a microprocessor positioned in a belt node or another similar intermediate device between the digital sensing electrodes and the medical device controller, to determine whether a digital sensing electrode has a compromised connection with the patient (e.g., is experiencing a falloff event) and compensate for a compromised connection. It should be noted that the following description of the process as shown in FIG. 6A is presented as being executed by the processor, but it should be noted that the processor and the digital front-end manager can operated in concert to execute the process as shown in FIG. 6A and described herein.

Referring now to FIG. 6A, the processor can receive 602 the electrode-specific digital signals from each of the digital sensing electrodes. For example, as described above, each digital sensing electrode can be configured to generate and output an electrode-specific digital signal and transmit or otherwise direct the signal to the processor. The processor can determine 604 a noise component for each of the electrode-specific digital signals. For example, the noise component can include any signal component outside of a specific frequency range of interest. The processor can be configured to filter the electrode-specific digital signals to identify, isolate, and attenuate noise components. In certain implementations, the processor can determine 604 a noise component using a similar process as that shown in FIG. 5B.

The processor can further analyze 606 the noise components from each of the electrode-specific digital signals to identify similar noise components or patterns in the noise components between individual digital sensing electrodes. In certain implementations, the processor can analyze 606 the noise components using a similar process as that shown in FIG. 5C. Based upon the analysis, the processor can determine 608 whether one or more of the digital sensing electrodes have a compromised connection. For example, if the electrode-specific digital signal for a particular digital sensing electrode is exhibiting an erratic noise pattern above a certain frequency or other similar threshold, the processor can determine 608 that the digital sensing electrode has a compromised connection with the patient.

Figure 6B:
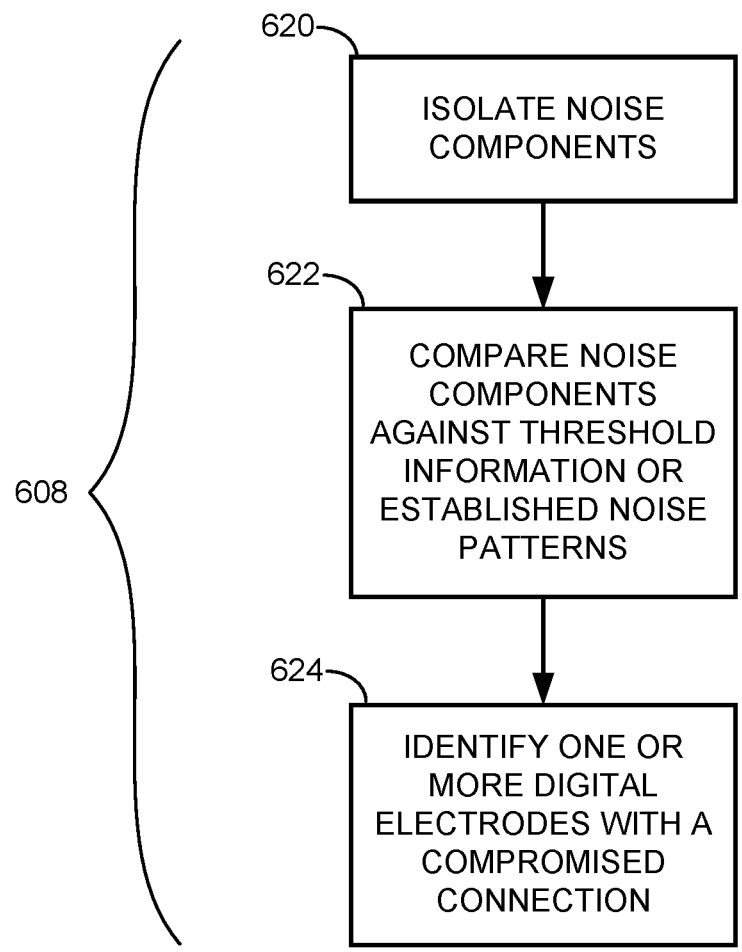
FIG. 6B depicts a sample implementation of one or more process steps as shown in FIG. 6A, in accordance with an example of the present disclosure.

FIG. 6B illustrates a sample process for determining 608 if a digital sensing electrode has a compromised connection with the patient. In certain implementations, the processor can isolate 620 and compare 622 the analyzed noise components against threshold information or established noise patterns. For example, an ambulatory medical device can include a pre-programmed or otherwise established set of threshold values for signal noise that are set by the device programmers prior to being received by the patient. Alternatively, or additionally, the ambulatory medical device can include a set of adaptive noise threshold values that are set when the patient initially receives the device and can be optionally updated as the device is worn by the patient. For example, to establish a set of patient-specific noise threshold values, the patient can be initially fitted with the ambulatory medical device and instructed to perform one or more initial physical activities. For example, the patient can be instructed to perform a six-minute walk test. During the test, the ambulatory medical device may record various noise values received from the digital sensing electrodes to establish a set of patient-specific noise patterns for normal use.

As further shown in FIG. 6B, the processor can identify 624 one or more digital electrodes with a compromised connection based upon the comparison of current noise components to the thresholds or established noise patterns as described above. For example, the noise thresholds can define 75 decibels as an upper limit of an uncompromised connection for a digital sensing electrode. Based upon the patient-specific noise patterns, for a particular patient, any noise that is measured, for example, more than 30% above the threshold can be considered indicative of a compromised connection. The decibel levels and percent variations as described herein are provided by way of example only and, depending upon the implementation and configuration of the ambulatory medical device, can vary.

Referring back to FIG. 6A, if the processor determines 608 that there are no digital sensing electrodes that have a compromised connection, the processor can continue to monitor 610 the patient regularly. If, however, the processor does determine 608 that there is at least one digital sensing electrode that has a compromised connection, the processor can ignore 612 the digital sensing electrode(s) with the compromised connection(s). For example, the processor can remove the digital sensing electrode with the compromised connection from consideration when pairing the digital sensing electrodes (e.g., as shown in FIG. 5A) and monitor 614 the patient with a reduced digital sensing electrode set. In some examples, the digital sensing electrode with the compromised connection can be ignored when generating a driven ground signal to be fed into the patient using, for example, a driven right leg circuit. In certain implementations, the processor can be configured to provide a notification to the patient and/or a caregiver associated with the patient of the compromised connection along with instructions of how to verify the position of the compromised digital sensing electrode.

For example, an ambulatory medical device can include four digital sensing electrodes such as those described above. During normal wear of the medical device by a patient, one of the digital electrodes (e.g., the front digital electrode) may be rolled away from the patient's skin, pull away from the patient's skin, or otherwise have a compromised connection with the patient's skin. Using the process as shown in FIG. 6A, a processor of the medical device can identify that the front digital electrode has a compromised connection with the patient. During cardiac monitoring the patient, the processor can ignore the electrode-specific digital signals from the front digital electrode rather than include those signals as inputs to, for example, the cardiac monitoring algorithm used to detect oncoming or occurring cardiac events being experienced by the patient. Additionally, as noted above, the processor can ignore the electrode-specific digital signals from the front digital electrode when summing the common mode signal and using the common mode signal for a driven ground to be fed into the patient. The processor can continue to monitor the electrode-specific digital signals received to determine whether the compromised connection has been corrected or otherwise addressed. In the event that the compromised connection has been corrected, the processor can include the electrode-specific digital signals from the front digital electrode (in this example) again in the analysis and processing of the electrode-specific digital signals from each of the digital sensing electrodes.

In some implementations, a compromised electrode connection can be determined by using a falloff detection technique as described above in regard to FIG. 4B. As noted above, electrode-skin contact can be assessed by passing a small excitation signal through the body and measuring the resultant response at one or more digital sensing electrodes. For example, as noted above, an excitation current source can be applied to the patient's skin at fixed frequency and the response measured locally at one or more digital sensing electrodes such as the digital sensing electrodes as described herein. A local oscillator (LO) at each digital sensing electrode can be phase matched to the excitation source. For example, both the excitation source and the LO can be set to about 800 Hz in order to perform synchronous detection. The LO can cause an amplifier to alternate between inverting and non-inverting to synchronously rectify the received signal. The result at each digital sensing electrode can be filtered and compared against, for example, a programmable threshold to assess electrode-skin contact. By including digital sensing electrodes as described herein, the electrode-skin contact can be determined independently for each of the digital sensing electrodes. The processor can then use, for example, a screen or other notification device to instruct the user to take some action such as adjust the position of the digital sensing electrode, apply gel to the electrode-skin interface, or take an additional action.

Figure 7:
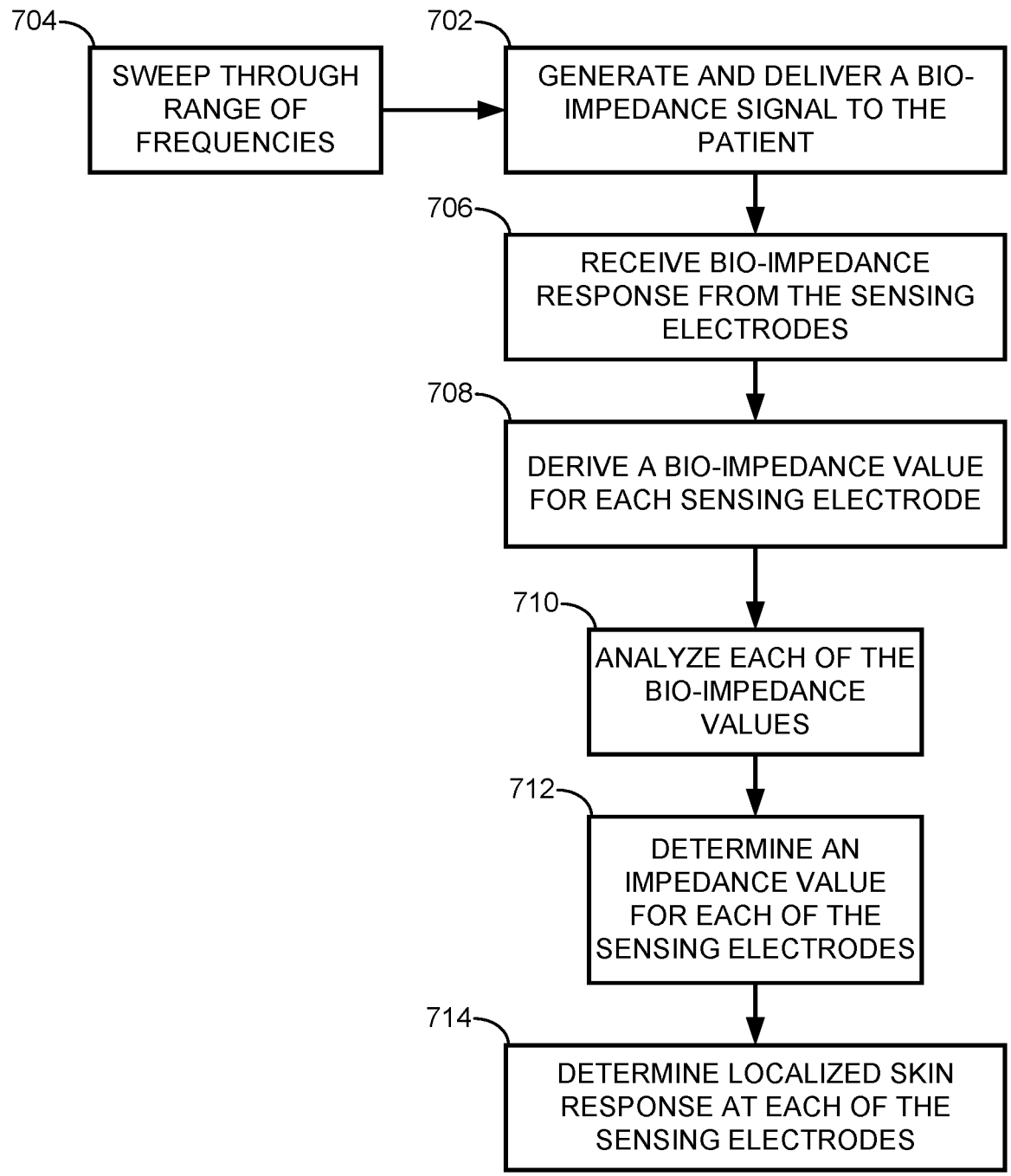
FIG. 7 depicts a sample process flow for determining skin condition, in accordance with an example of the present disclosure.

In addition to monitoring and accommodating noise as described above, the digital sensing electrode and front-end features as described herein can be used to provide additional functionality for an ambulatory medical device. For example, FIG. 7 illustrates a sample process flow for determining a localized skin response for a patient at one or more digital sensing electrode locations. Based upon this information, a digital front-end management component such as digital front-end manager 213 of medical device controller 200 as described above can be configured to work in concert with a processor, such as processor 218, to determine information related to the skin such as hydration levels and how signal quality may be impacted by the patient's skin.

The process of FIG. 7 is described below as being executed by the processor. Alternatively or in addition, the processor and the digital front-end manager can be operated in concert to execute the process as shown in FIG. 7 and described herein.

Referring now to FIG. 7, the processor can generate 702 and deliver a bio-impedance signal to the patient. This bio-impedance signal can include a specific frequency signal transmitted by the digital sensing electrodes to the patient. In some examples, the bio-impedance signal can be transmitted to the patient by other electrodes such as therapy electrodes if included in the ambulatory medical device.

In some examples, the processor can sweep 704 through a range of frequencies when generating the bio-impedance signal such that the signal transmitted to the patient is transmitted at multiple frequencies. For example, the bio-impedance signal can include a signal driven onto the patient's body and sweeping in frequency from about 700 Hz to about 200 kHz. In some examples, the bio-impedance signal can include a frequency sweep from about 50 Hz to about 500 kHz. In other examples, the bio-impedance signal can include a frequency sweep that includes signals in the megahertz range such as from about 1 MHz to about 25 MHz.

The processor can receive 706 a bio-impedance response from each of the digital sensing electrodes and derive 708 a bio-impedance value for each digital sensing electrode. For example, the bio-impedance value can include frequencies each of the digital sensing electrodes detected and the strength of the detected signals. The processor can analyze 710 each of the bio-impedance values for each of the digital sensing electrodes and determine 712 an impedance value for each of the digital sensing electrodes. Based upon this information, the processor can determine 714 a localized skin response at each of the digital sensing electrode locations. For example, the localized skin response can include a hydration level for the skin proximate the digital sensing electrode location. For example, the processor can be configured to measure a patient's electrodermal activity (EDA) based upon the received bio-impedance response. EDA holds that skin resistance varies with the state of sweat glands in the skin as well as any present surface sweat or other conductive fluids such as a conductive gel. Based upon measured other otherwise detected changes in the impedance values at each of the digital electrodes, the process can determine the localized skin response. In certain implementations, this localized skin response can be based on a baseline skin response that was established when the patient was first prescribed the ambulatory medical device. For example, when first fitted, the digital sensing electrodes of the ambulatory medical device may have a conductive gel applied to ensure optimal skin hydration at the skin-electrode interface. The patient may then be instructed to complete a physical task such as complete a six-minute walk test. During the test, hydration levels at each of the digital sensing electrodes can be measured using, for example, a similar process as that shown in FIG. 7 and described above. Based upon the initial hydration measurements, a baseline set of skin impedance response values can be determined for the patient for each of the frequencies associated with the bio-impedance signal. By comparing measured bio-impedance responses to the baseline set of skin impedance response values, the processor can determine the impedance value 712 for the patient. For example, the impedance value can include a value between 0.0 and 1.0 that is indicative of the current bio-impedance response as compared to the baseline response values. For example, a value of 1.0 can indicate that the current bio-impedance response is equal to the baseline response (e.g., an optimum hydration level). A value of 0.0 can indicate that there is no response. In certain implementations, the values assigned to the current bio-impedance response can scale linearly between 0.0 and 1.0 as the bio-impedance response increases from no response (0.0) to optimum hydration (1.0).

Based upon the determined bio-impedance response and hydration information, the processor can provide information to the patient or initiate additional actions. For example, the processor can provide a notification to the patient (e.g., through a display integrated into the ambulatory medical device) to apply a conductive gel or otherwise moisturize their skin near the digital sensing electrodes to improve skin hydration and signal quality.

In some examples, the processor can also generate an impedance model for the patent for each of the digital sensing electrodes based upon the localized skin response. This skin model can be used to adjust signals received from the digital sensing electrodes (e.g., to compensate for a weak signal due to a dry skin-electrode interface), estimate hydration levels at other portions of the patient's skin (e.g., at positions adjacent to therapy electrodes), and perform other similar modeling tasks. Additionally, this skin model can be used to analyze trends related to hydration levels for example, by measuring and modeling changes in skin impedance as a result of hydration over time, a doctor or other clinician can see a potential correlation between skin hydration and other factors such as time of year, patient medications and/or dosage information, changes in diet, changes in exercise routines, and other similar factors.

In certain implementations, the bio-impedance response can be analyzed using a demodulation technique such as a quadrature detection algorithm that builds on the utilization of a quadrature signal. As noted above, an excitation source varies its frequency over a known range (e.g., from about 700 Hz to about 200 kHz) to produce the bio-impedance signal. A bio-impedance response can be measured at each of the digital sensing electrodes and digitized. The signal can be passed through multiple low-pass filters, and magnitude and phase information for the bio-impedance response can be obtained over the range of frequencies. Based upon the magnitude and phase information, a bio-impedance profile can be created. The information contained in the profile can be used to assess electrode falloff, electrode-skin interface model parameters and interface quality, skin information such as hydration information, and other related information as measured over time.

Figure 8A:
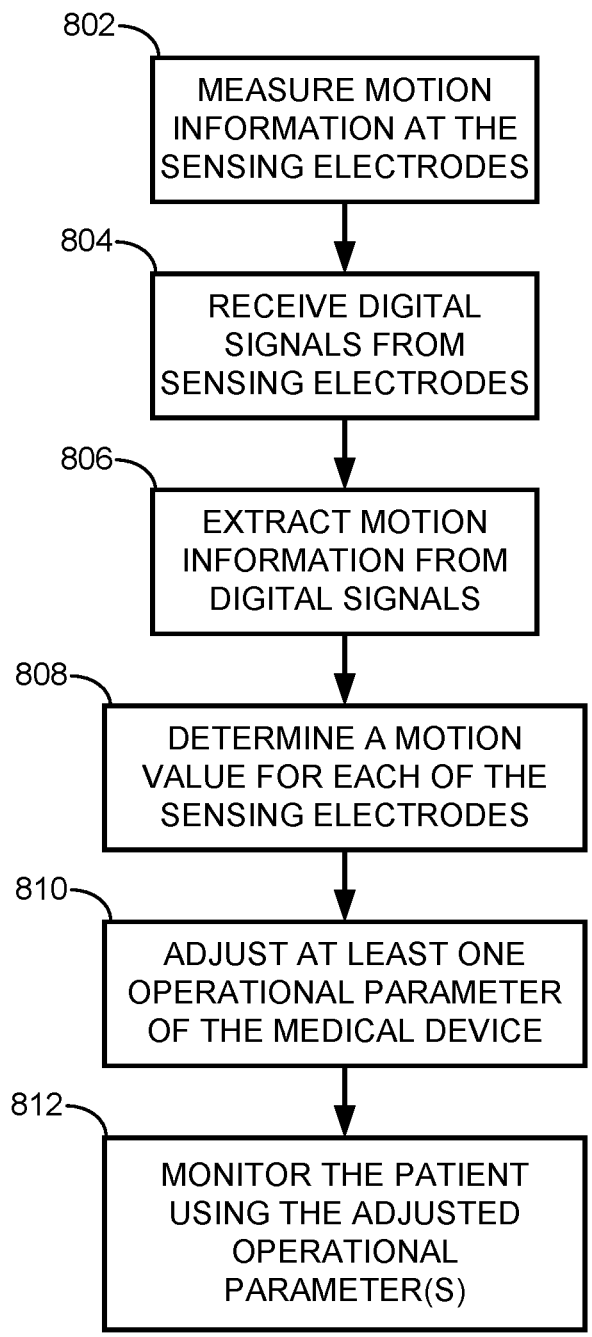
FIG. 8A depicts a sample process flow for updating patient monitoring parameters in response to determining motion at one or more digital sensing electrodes, in accordance with an example of the present disclosure.
Figure 8B:
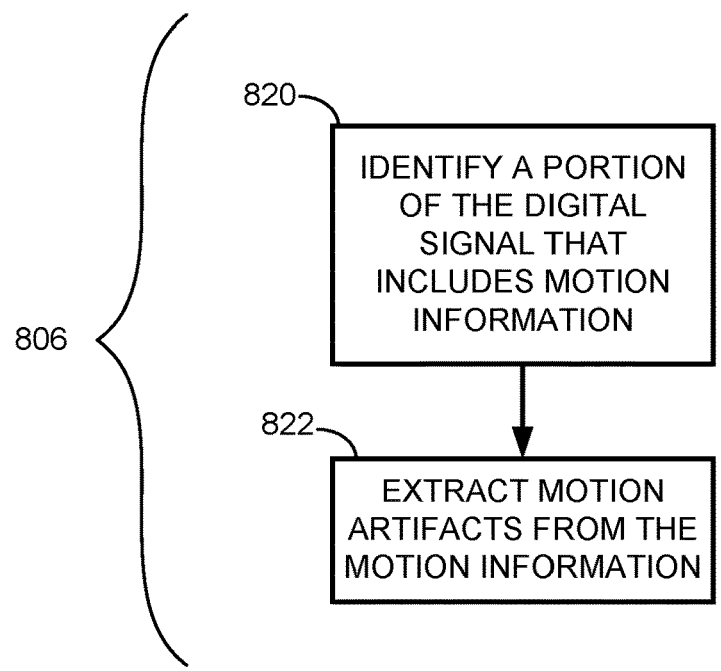
FIGS. 8B and 8C depict sample implementations of one or more process steps as shown in FIG. 8A, in accordance with an example of the present disclosure.

FIG. 8A illustrates a process flow for determining motion information and artifacts in digital sensing electrode signals and adjusting the monitoring of the patient to accommodate for the motion information. The motion information and artifacts are local to the respective digital sensing electrode as the motion sensors for this purpose are located proximate to the skin-contacting electrode surfaces of the digital sensing electrodes as shown above in connection with FIG. 1B. For example, each of the digital sensing electrodes can include a local motion sensor such as a three-axis accelerometer configured to measure 802 localized motion information for each digital sensing electrode. This localized motion information can be transmitted to a processor, such as digital front-end manager 213 working in concert with processor 218 of medical device controller 200 as described above, for additional analysis and processing. For example, the processor can receive 804 the electrode-specific digital signals from each of the digital sensing electrodes and extract 806 the motion information. For example, FIG. 8B illustrates a sample process for extracting 806 the motion information. As shown in FIG. 8B, the processor can identify 820 a portion of the electrode-specific digital signal that includes motion information generated by the motion sensors. For example, the processor can identify 820 a portion of the electrode-specific digital signals that include data formatted to include motion information or a portion of the signals that include packet header or other similar identification information indicating the signal include motion information. The processor can extract 822 motion artifacts from the motion information for further processing.

Referring back to FIG. 8A, the processor can analyze the motion information to determine 808 a motion value for each of the digital sensing electrodes. For example, the motion value can include an indication of type of motion, duration of motion, and severity of motion. In certain implementations, the processor can compare the motion values against certain motion thresholds to determine a likelihood that the motion is impacting signal quality or otherwise affecting the output of the digital sensing electrodes. In certain implementations, the processor can remove some of the effect of motion artifacts by applying signal processing techniques. For example, depending upon the output data rate and latency requirements, data containing both the ECG signals and some level of motion artifacts can be processed to improve signal quality. In some examples, adaptive filtering and stationary wavelet transform techniques can be applied to reduce and/or remove motion artifact effects. One such adaptive filtering technique can correct or otherwise improve an ECG signal containing motion artifacts by using a reference signal correlated in the same manner with the ECG signal. Filter and/or model parameters can be automatically adjusted using known or previously characterized system noise information to generate the reference signal. Additionally, the output of any accelerometers or other motion detectors at each digital sensing electrode can be up-sampled using, for example, a linear interpolation method to obtain acceleration module vectors. The acceleration module vectors can be analyzed to identify timing segments where motion artifacts were likely introduced to the ECG signals and the ECG signals can be decomposed using, for example, stationary wavelet transforms to remove any unwanted noise artifact caused by motion.

Figure 8C:
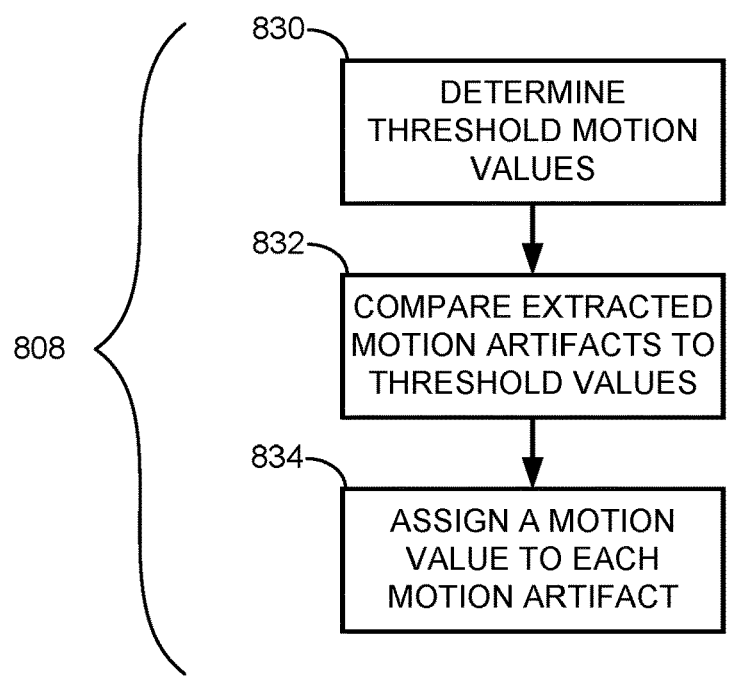

Referring back to the figures, FIG. 8C illustrates a sample process for determining 808 a motion value for each of the digital sensing electrodes. As shown in FIG. 8C, the processor can determine 830 threshold motion values. For example, the processor can load a set of pre-programmed thresholds determined prior to the ambulatory medical device being prescribed to a patient. Alternatively, or additionally, the processor can load a set of patient-specific threshold motion values that were determined, for example, when the patient was first prescribed the ambulatory medical device. Similar to the example above regarding patient-specific noise patterns, a patient can be initially fitted with an ambulatory medical device and instructed to perform one or more physical tasks such as complete a six-minute walk test. During the physical activity, the processor can receive motion information from each of the motion detectors in the digital electrodes as described herein and determine a set of patient-specific threshold motion values.

As further shown in FIG. 8C, the processor can compare 832 the extracted motion artifacts to the threshold values. Based upon the comparison, the processor can assign 834 or otherwise determine a motion value for each motion artifact. For example, the processor can compare 832 the magnitude of the motion artifact to the stored thresholds. If the magnitude of the motion artifact exceeds the threshold by a certain amount, the processor can assign 834 a motion value between 0.0 and 1.0 to the motion artifact, the motion value indicative of the amount the motion artifact exceeds the threshold. For example, a motion value of 0.1 can indicate that the motion artifact exceeded the threshold by 10%. Similarly, a value of 1.0 can indicate that the motion artifact exceeded the threshold by 100% or more. Thus, the processor can assign 834 a motion value for each motion artifact based upon the established threshold motion values.

Referring again to FIG. 8A, if the processor determines that the motion information (e.g., the extracted motion artifacts as described above) is impacting the signal quality of the digital sensing electrode, the processor can adjust 810 at least one operational parameter of the medical device and monitor 812 the patient using the adjusted operational parameters. For example, the processor can ignore the output of a digital sensing electrode having a high motion value until the motion value falls below a certain threshold.

In some examples, the processor can identify noise artifacts in the electrode-specific digital signals and store the artifact information for later analysis. The artifact information can be used by the processor when generating ECG metric information to improve the quality of the ECG metric information.

The teachings of the present disclosure can be generally applied to external medical monitoring and/or treatment devices. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other caregiver provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., electrocardiogram (ECG) information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate, heart rate variability, premature ventricular complex (PVC) burden or counts, atrial fibrillation burden, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

Figure 9A:
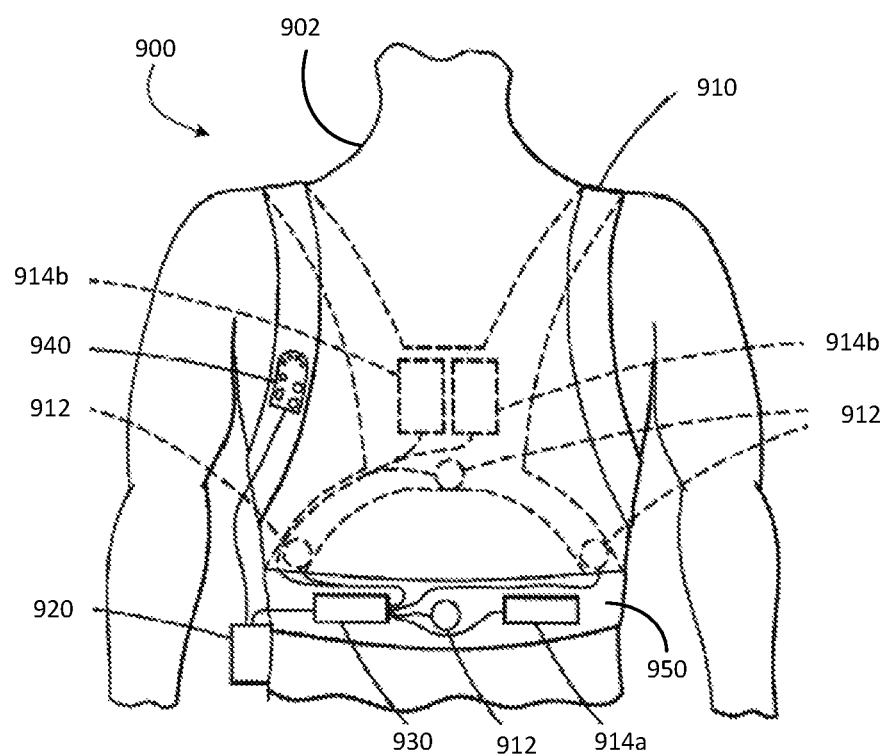
FIGS. 9A-9D depict sample ambulatory medical devices that include digital sensing electrodes, in accordance with an example of the present disclosure.

FIG. 9A illustrates an example medical device 900 that is external, ambulatory, and wearable by a patient 902, and configured to implement one or more configurations described herein. For example, the medical device 900 can be a non-invasive medical device configured to be located substantially external to the patient. Such a medical device 900 can be, for example, an ambulatory medical device that is capable of and designed for moving with the patient as the patient goes about his or her daily routine. For example, the medical device 900 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 900 can include one or more of the following: a garment 910, one or more digital sensing electrodes 912 (e.g., digital sensing electrodes as described herein), one or more therapy electrodes 914a and 914b (collectively referred to herein as therapy electrodes 914), a medical device controller 920, a connection pod 930, a patient interface pod 940, a belt 950, or any combination of these. In some examples, at least some of the components of the medical device 900 can be configured to be affixed to the garment 910 (or in some examples, permanently integrated into the garment 910), which can be worn about the patient's torso.

The medical device controller 920 can be operatively coupled to the digital sensing electrodes 912, which can be affixed to the garment 910, e.g., assembled into the garment 910 or removably attached to the garment, e.g., using hook and loop fasteners (e.g., fastener 108 as described above in regard to FIG. 1A). In some implementations, the digital sensing electrodes 912 can be permanently integrated into the garment 910. The medical device controller 920 can be operatively coupled to the therapy electrodes 914. For example, the therapy electrodes 914 can also be assembled into the garment 910, or, in some implementations, the therapy electrodes 914 can be permanently integrated into the garment 910.

Component configurations other than those shown in FIG. 9A are possible. For example, the digital sensing electrodes 912 can be configured to be attached at various positions about the body of the patient 902. The digital sensing electrodes 912 can be operatively coupled to the medical device controller 920 through the connection pod 930. In some implementations, the digital sensing electrodes 912 can be adhesively attached to the patient 902. In some implementations, the digital sensing electrodes 912 and at least one of the therapy electrodes 914 can be included on a single integrated patch and adhesively applied to the patient's body.

The digital sensing electrodes 912 can be configured to detect one or more cardiac signals. Examples of such signals include ECG signals and/or other sensed cardiac physiological signals from the patient. In certain examples, as described herein, the digital sensing electrodes 912 can include additional components such as accelerometers, acoustic signal detecting devices, and other measuring devices for recording additional parameters. For example, the digital sensing electrodes 912 can also be configured to detect other types of patient physiological parameters and acoustic signals, such as tissue fluid levels, cardio-vibrations, lung vibrations, respiration vibrations, patient movement, etc.

In some examples, the therapy electrodes 914 can also be configured to include sensors configured to detect ECG signals as well as other physiological signals of the patient. The connection pod 930 can, in some examples, include a signal processor configured to amplify, filter, and digitize these cardiac signals prior to transmitting the cardiac signals to the medical device controller 920. One or more of the therapy electrodes 914 can be configured to deliver one or more therapeutic defibrillating shocks to the body of the patient 902 when the medical device 900 determines that such treatment is warranted based on the signals detected by the digital sensing electrodes 912 and processed by the medical device controller 920. Example therapy electrodes 914 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 914 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 9B:
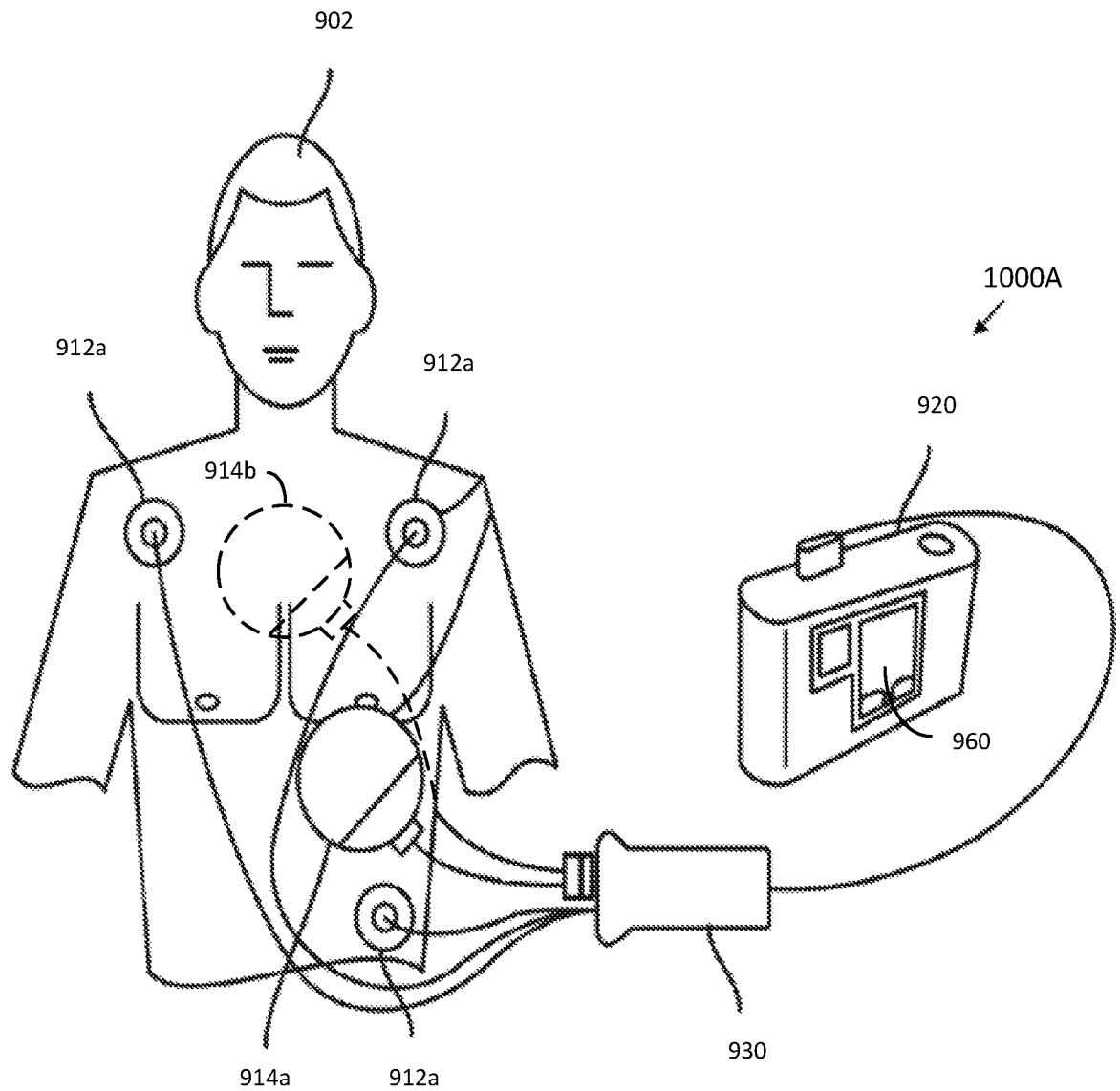

FIG. 9B illustrates a hospital wearable defibrillator 1000A that is external, ambulatory, and wearable by a patient 902. Hospital wearable defibrillator 1000A can be configured in some implementations to provide pacing therapy, e.g., to treat bradycardia, tachycardia, and asystole conditions. The hospital wearable defibrillator 1000A can include one or more digital sensing electrodes 912a, one or more therapy electrodes 914a and 914b, a medical device controller 920 and a connection pod 930. For example, each of these components can be structured and function as like number components of the medical device 900. For example, the electrodes 912a, 914a, 914b can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 914a attaches to the front of the patient's torso to deliver pacing or defibrillating therapy. Similarly, the back adhesively attachable therapy electrode 914b attaches to the back of the patient's torso. In an example scenario, at least three ECG adhesively attachable digital sensing electrodes 912a can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 960 can be configured to interact with a user other than the patient, e.g., a nurse, for device-related functions such as initial device baselining, setting and adjusting patient parameters, and changing the device batteries.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 9B.

Figure 9C:
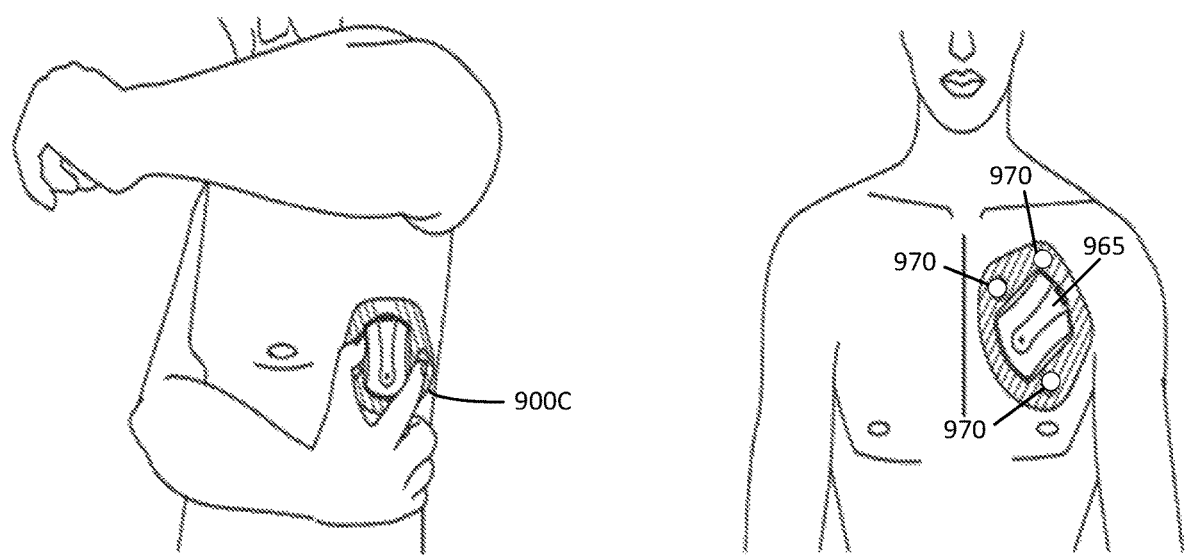
Figure 9D:
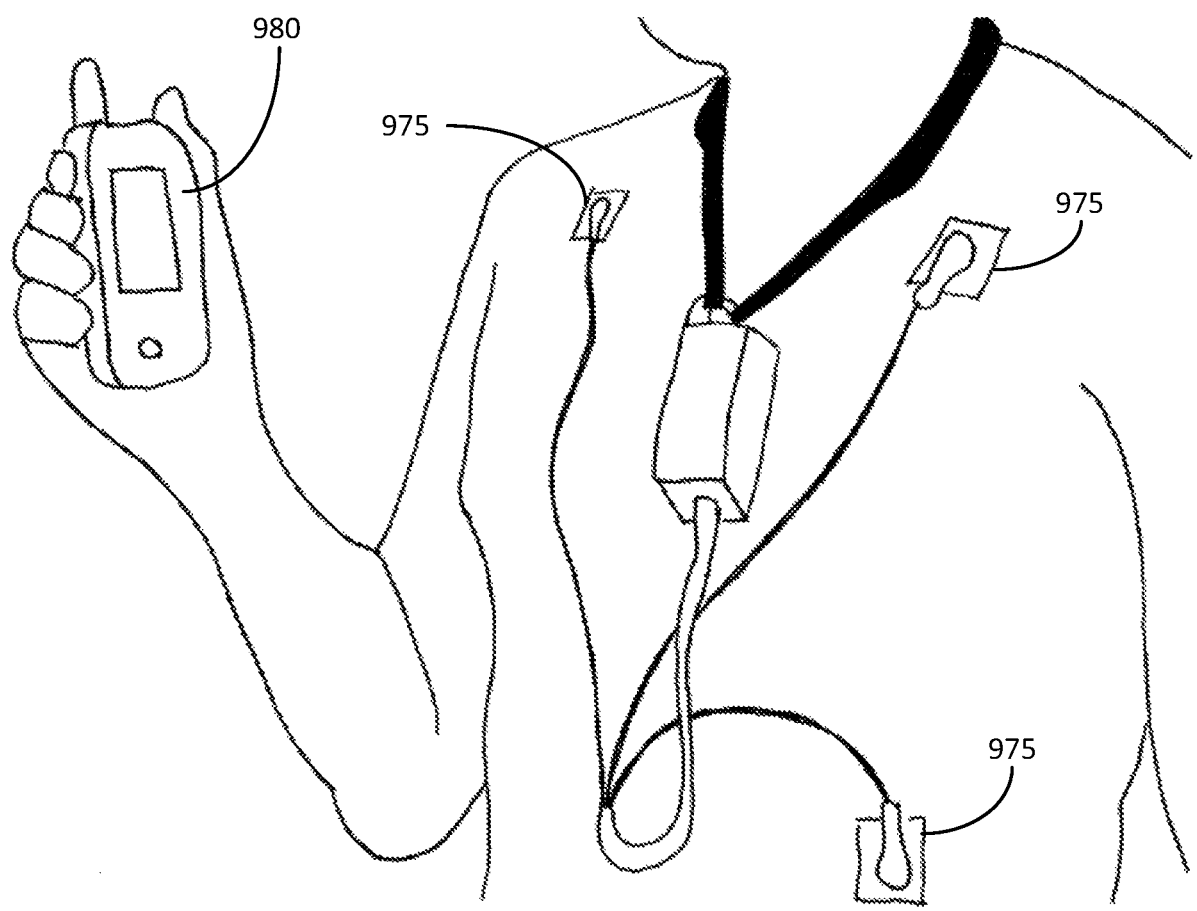

FIGS. 9C and 9D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 9C, an example wearable patient monitoring device 900C can include tissue fluid monitors 965 that use radio frequency (RF) based techniques to assess fluid levels and accumulation in a patient's body tissue. Such tissue fluid monitors 965 can be configured to measure fluid content in the lungs, typically for diagnosis and follow-up of pulmonary edema or lung congestion in heart failure patients. The tissue fluid monitors 965 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 900C may be a cardiac monitoring device that also includes digital sensing electrodes 970 for sensing ECG activity of the patient. Device 900C can pre-process the ECG signals via one or more ECG processing and/or conditioning circuits such as an ADC, operational amplifiers, digital filters, signal amplifiers under control of a microprocessor. Device 900C can transmit information descriptive of the ECG activity and/or tissue fluid levels via a network interface to a remote server for analysis.

Referring to FIG. 9D, another example wearable cardiac monitoring device can be attached to a patient via at least three adhesive digital cardiac sensing electrodes 975 disposed about the patient's torso. The cardiac devices illustrated in FIGS. 9C and 9D are used in cardiac telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause (s), and/or heart palpitations. For example, such patients may be prescribed a cardiac monitoring device for an extended period of time, e.g., 10 to 30 days, or more. In some mobile cardiac telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or caregivers, and feedback provided to the patient and/or a designated caregiver via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), tissue fluids, among others.

In some examples, the devices described herein (e.g., FIGS. 9A-D) can communicate with a remote server via an intermediary device 980 such as that shown in FIG. 9D. For instance, devices such as shown in FIGS. 9A-D can be configured to include a network interface communications capability as described herein in reference to, for example, FIG. 2.

Figure 10:
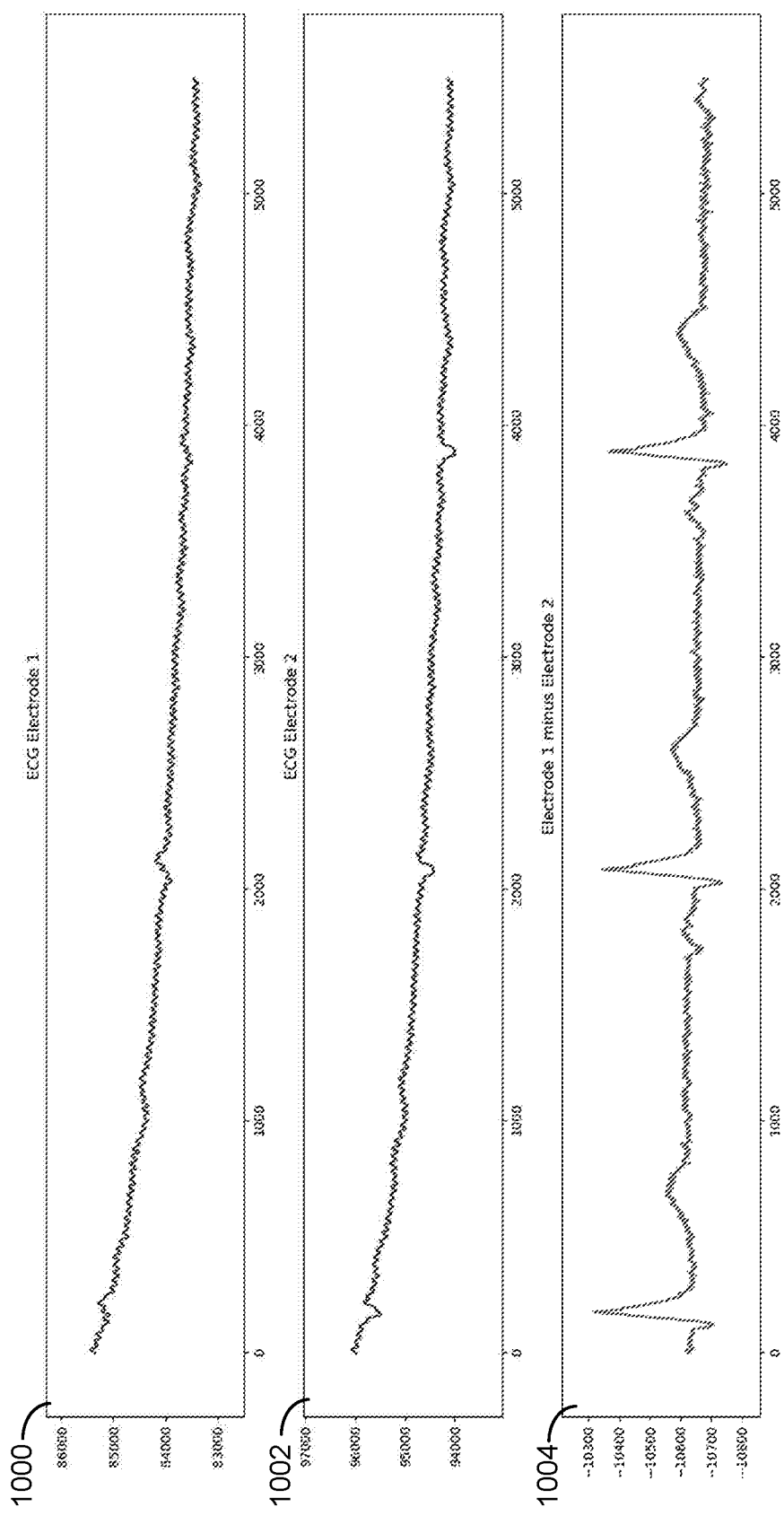
FIG. 10 illustrates sample digital sensing electrode signals, in accordance with an example of the present disclosure.

The techniques and processes as described herein have been tested in a series of experiments. For example, a human patient was fitted with an ambulatory medical device including a set of digital sensing electrodes similar to those as described above in reference to FIGS. 4A and 4B. The patient's ECG signal was collected by the digital electrodes and monitored by a monitoring device. FIG. 10 illustrates a sample output of the ambulatory medical device including the digital sensing electrodes. The top graph 1000 represents the measured electrical activity at a first digital sensing electrode. The middle graph 1002 represents the measured electrical activity at a second digital sensing electrode. The bottom graph 1004 represents the ECG activity for the patient as measured by the combined pair of the first digital sensing electrode and the second digital sensing electrode. As described herein, the ECG activity for a pair can be determined by inverting one of the measured electrical signals (in this example, the second digital sensing electrode output is inverted) and the two outputs are summed. As shown in the bottom graph 1004, the resulting waveform includes a series of identifiable QRS waves indicative of the patient's heart rate.

In graphs 1000, 1002, and 1004 of FIG. 10, the x-axis represents time measured in milliseconds and the y-axis represents samples-per-second of the ADCs associated with each of the digital sensing electrodes.

In an example, a patient may have been prescribed an ambulatory medical device such as a WCD to wear for an extended period of time (e.g., 30 days). The patient may be active and exercise regularly. As a result, the digital sensing electrodes of the WCD can experience regular noise as a result of the patient's movement or, in some instances, experience falloff events. The WCD can include a digital front-end with digital electrodes such as those described herein such that the electrode pairs can be dynamically updated to accommodate motion related noise and artifacts as well as compensate for falloff events.

In a similar example, a patient may be wearing an ill-fitting garment for their WCD that results in poor skin contact by the digital sensing electrodes. In such an example, even at rest, the digital sensing electrodes may be providing a noisy signal to the WCD controller. The controller can update the digital sensing electrode pairs while providing a notification to the patient to check or adjust the placement of the digital sensing electrodes.

In yet another example, a patient may be experiencing dry skin at the locations of the digital sensing electrodes. By monitoring bio-impedance signals, the WCD controller can determine skin hydration levels and how those hydration levels are impacting signal quality. The WCD controller may provide the patient with a notification to apply, for example, conductive gel or another similar moisturizing product to their skin and/or to the digital sensing electrodes to increase skin hydration and improve signal quality.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any example can be combined with one or more features of any other example.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. An ambulatory medical device for monitoring a patient's cardiac activity using a digital front-end, the ambulatory medical device comprising:
    a plurality of sensing electrodes configured to be coupled to a patient and to detect one or more ECG signals of the patient, wherein each of the plurality of sensing electrodes has electrode-specific digital signal circuitry disposed within an electrode housing, the electrode-specific digital signal circuitry comprising:
        at least one contact surface coupled to the electrode housing and configured to be coupled to the patient and collect electrical signals from the patient,
        a digital converter disposed within the electrode housing, operably connected to the at least one contact surface and configured to convert the collected electrical signals, collected via the at least one contact surface, to an electrode-specific digital signal, and
        at least one electrode processor disposed within the electrode housing, operably connected to the digital converter and configured to control a sampling rate of the digital converter; and
    one or more processors operably coupled to the plurality of sensing electrodes and being configured to receive the electrode-specific digital signal from each of the plurality of sensing electrodes, analyze each of the electrode-specific digital signals, determine one or more sensing electrode pairs based upon analysis of each of the electrode-specific digital signals, and monitor each of the one or more sensing electrode pairs for ECG activity of the patient.

2. The ambulatory medical device of claim 1, the one or more processors being configured to:

receive the electrode-specific digital signal from each of the plurality of sensing electrodes; and determine a noise component for each of the electrode-specific digital signals, wherein each of the plurality of sensing electrodes has an associated noise component.

3. The ambulatory medical device of claim 2, the one or more processors being further configured to:

analyze each of the noise components for each of the plurality of sensing electrodes to determine whether one or more sensing electrodes of the plurality of sensing electrodes has a physically compromised connection with the patient;

ignore at least one of the one or more sensing electrodes having the physically compromised connection with the patient, thereby resulting in a reduced set of sensing electrodes; and monitor ECG activity of the patient using the reduced set of sensing electrodes.

4. The ambulatory medical device of claim 2, the one or more processors being further configured to:

analyze each of the noise components of the plurality of sensing electrodes;

generate electrode matching information for each sensing electrode of the plurality of sensing electrodes based upon analysis of each of the noise components;

determine the one or more sensing electrode pairs based upon the electrode matching information; and monitor each of the one or more sensing electrode pairs for the ECG activity of the patient.

5. The ambulatory medical device of claim 1, the one or more processors being further configured to determine a gain adjustment for one or more of the plurality of sensing electrodes to improve signal quality of at least one of the one or more sensing electrode pairs.

6. The ambulatory medical device of claim 1, wherein the analysis of each of the electrode-specific digital signals comprises one or more of analysis of a signal strength ranking for each of the plurality of sensing electrodes and analysis of a signal-to-noise ratio for each of the plurality of sensing electrodes.

7. The ambulatory medical device of claim 1, wherein the ECG activity comprises one or more ECG metrics derived from the one or more ECG signals of the patient, the one or more ECG metrics comprise at least one of heart rate, heart rate variability, PVC burden or counts, atrial fibrillation burden, pauses, heart rate turbulence, QRS height, QRS width, changes in a size or shape of morphology of the ECG signals, cosine R-T, artificial pacing, QT interval, QT variability, T wave width, T wave alternans, T-wave variability, and ST segment changes.

8. The ambulatory medical device of claim 1, wherein the digital converter comprises an analog to digital converter (ADC) configured to receive an analog electrical signal produced by the patient and convert the analog electrical signal to the electrode-specific digital signal.

9. The ambulatory medical device of claim 8, wherein the digital converter is configured to sample the analog electrical signal at a dynamically adjustable sampling rate controlled by the one or more processors.

10. The ambulatory medical device of claim 9, the one or more processors being further configured to generate a common timing signal for each digital converter such that the plurality of sensing electrodes are synchronized.

11. The ambulatory medical device of claim 1, wherein the ECG activity comprises one or more ECG metrics derived from the collected electrical signals from the patient.

12. The ambulatory medical device of claim 1, wherein the one or more processors being configured to determine the one or more sensing electrode pairs comprises the one or more processors being configured to:

generate electrode matching information for each sensing electrode of the plurality of sensing electrodes based upon analysis of each of the electrode-specific digital signals; and determine the one or more sensing electrode pairs based upon the electrode matching information.

13. The ambulatory medical device of claim 12, wherein the electrode matching information comprises one or more of a signal strength ranking for each of the plurality of sensing electrodes and a signal-to-noise ratio for each of the plurality of sensing electrodes.

14. The ambulatory medical device of claim 12, the one or more processors being further configured to:

receive an updated electrode-specific digital signal for each sensing electrode of the plurality of sensing electrodes; and determine one or more updated sensing electrode pairs based upon the updated electrode-specific digital signal for each sensing electrode of the plurality of sensing electrodes.

15. The ambulatory medical device of claim 14, the one or more processors being further configured to:

analyze the updated electrode-specific digital signal for each sensing electrode of the plurality of sensing electrodes; and determine the one or more updated sensing electrode pairs based upon the analysis of the updated electrode-specific digital signal for each sensing electrode of the plurality of sensing electrodes.

16. The ambulatory medical device of claim 15, the one or more processors being further configured to:

generate updated electrode matching information for each sensing electrode of the plurality of sensing electrodes based upon the analysis of the updated electrode-specific digital signal for each sensing electrode of the plurality of sensing electrodes; and determine the one or more updated sensing electrode pairs based upon the updated electrode matching information.

* * * * *